United States Patent
Marmur et al.

(10) Patent No.: US 10,485,684 B2
(45) Date of Patent: Nov. 26, 2019

(54) ENDOVASCULAR STENT-GRAFT WITH FATIGUE-RESISTANT LATERAL TUBE

(71) Applicant: ENDOSPAN LTD., Herzilyia Pituach (IL)

(72) Inventors: Yaniv Marmur, Yokneam Moshava (IL); Nir Shalom Nae, Binyamina Givat Ada (IL); Alon Shalev, Ra'anana (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 72 days.

(21) Appl. No.: 15/105,106

(22) PCT Filed: Dec. 16, 2015

(86) PCT No.: PCT/IL2015/051221
§ 371 (c)(1),
(2) Date: Jun. 16, 2016

(87) PCT Pub. No.: WO2016/098113
PCT Pub. Date: Jun. 23, 2016

(65) Prior Publication Data
US 2017/0273809 A1 Sep. 28, 2017

Related U.S. Application Data

(60) Provisional application No. 62/093,497, filed on Dec. 18, 2014.

(51) Int. Cl.
*A61F 2/91* (2013.01)
*A61F 2/07* (2013.01)
(Continued)

(52) U.S. Cl.
CPC .................. *A61F 2/91* (2013.01); *A61F 2/07* (2013.01); *A61F 2/848* (2013.01); *A61F 2/89* (2013.01); *A61F 2002/061* (2013.01)

(58) Field of Classification Search
CPC .... A61F 2/91; A61F 2/07; A61F 2/848; A61F 2/89; A61F 2002/061
See application file for complete search history.

(56) References Cited

U.S. PATENT DOCUMENTS

| 4,180,613 A | 12/1979 | Vas Siliou |
|---|---|---|
| 4,355,426 A | 10/1982 | MacGregor |

(Continued)

FOREIGN PATENT DOCUMENTS

| CA | 2 497 704 | 3/2004 |
|---|---|---|
| CN | 1194577 | 9/1998 |

(Continued)

OTHER PUBLICATIONS

"E-vita® open plus" product brochure (JOTEC GmbH, Hechingen, Germany), 2010.

(Continued)

*Primary Examiner* — Thomas M McEvoy
(74) *Attorney, Agent, or Firm* — Sughrue Mion, PLLC

(57) ABSTRACT

A stent-graft (20) comprises strut members (30) and a graft member (32), which is fixed to the strut members (30). The strut members (30) and the graft member (32) are arranged so as to define, when the stent-graft (20) is in a radially-expanded state: a main tube (40), which is shaped so as to define a main lumen (42); and a lateral tube (50), which (a) has (i) a distal end (52) and (ii) a proximal end (54) that is joined to a lateral wall (56) of the main tube (40) at a junction (60), (b) is shaped so as to define a lateral lumen (62) that is in fluid communication with the main lumen (42), and (c) defines a central longitudinal axis (64). The strut members (30) that define the lateral tube (50) are shaped so as to define two to four non-contiguous arcuate members (70), which (a) are centered around the central (Continued)

longitudinal axis (64), and (b) collectively subtend at least 150 degrees around the central longitudinal axis (64).

39 Claims, 11 Drawing Sheets

(51) Int. Cl.
*A61F 2/89* (2013.01)
*A61F 2/06* (2013.01)
*A61F 2/848* (2013.01)

(56) References Cited

U.S. PATENT DOCUMENTS

| | | | |
|---|---|---|---|
| 4,505,767 A | 3/1985 | Quin | |
| 4,562,596 A | 1/1986 | Kornberg | |
| 4,577,631 A | 3/1986 | Kreamer | |
| 4,617,932 A | 10/1986 | Kornberg | |
| 4,665,906 A | 5/1987 | Jervis | |
| 4,739,762 A | 4/1988 | Palmaz | |
| 4,787,899 A | 11/1988 | Lazarus | |
| 4,816,339 A | 3/1989 | Tu et al. | |
| 4,878,906 A | 11/1989 | Lindemann et al. | |
| 4,886,062 A | 12/1989 | Wiktor | |
| 4,938,740 A | 7/1990 | Melbin | |
| 4,969,458 A | 11/1990 | Wiktor | |
| 5,042,707 A | 8/1991 | Taheri | |
| 5,064,435 A | 11/1991 | Porter | |
| 5,104,404 A | 4/1992 | Wolff | |
| 5,122,136 A | 6/1992 | Guglielmi et al. | |
| 5,129,910 A | 7/1992 | Phan et al. | |
| 5,133,732 A | 7/1992 | Wiktor | |
| 5,192,256 A | 3/1993 | Ryan | |
| 5,192,286 A | 3/1993 | Phan et al. | |
| 5,234,448 A | 8/1993 | Wholey et al. | |
| 5,383,926 A | 1/1995 | Lock et al. | |
| 5,425,739 A | 6/1995 | Jessen | |
| 5,425,765 A | 6/1995 | Tiefenbrun et al. | |
| 5,439,446 A | 8/1995 | Barry | |
| 5,456,694 A | 10/1995 | Marin et al. | |
| 5,486,183 A | 1/1996 | Middleman et al. | |
| 5,507,769 A | 4/1996 | Marin et al. | |
| 5,509,923 A | 4/1996 | Middleman et al. | |
| 5,522,880 A | 6/1996 | Barone et al. | |
| 5,527,322 A | 6/1996 | Klein et al. | |
| 5,549,662 A | 8/1996 | Fordenbacher | |
| 5,554,181 A | 9/1996 | Das | |
| 5,556,413 A | 9/1996 | Lam | |
| 5,562,724 A | 10/1996 | Vorwerk et al. | |
| 5,575,818 A | 11/1996 | Pinchuk | |
| 5,607,445 A | 3/1997 | Summers | |
| 5,613,974 A | 3/1997 | Andreas et al. | |
| 5,632,746 A | 5/1997 | Middleman et al. | |
| 5,632,763 A | 5/1997 | Glastra | |
| 5,632,772 A | 5/1997 | Alcime et al. | |
| 5,639,278 A | 6/1997 | Dereume et al. | |
| 5,643,340 A | 7/1997 | Nunokawa | |
| 5,653,743 A | 8/1997 | Martin | |
| 5,676,696 A | 10/1997 | Marcade | |
| 5,676,697 A | 10/1997 | McDonald | |
| 5,693,084 A | 12/1997 | Chuter | |
| 5,728,134 A | 3/1998 | Barak | |
| 5,749,825 A | 5/1998 | Fischell et al. | |
| 5,749,879 A | 5/1998 | Middleman et al. | |
| 5,755,770 A | 5/1998 | Ravenscroft | |
| 5,755,771 A | 5/1998 | Penn et al. | |
| 5,755,774 A | 5/1998 | Pinchuk | |
| 5,755,777 A | 5/1998 | Chuter | |
| 5,755,781 A | 5/1998 | Jayaraman | |
| 5,769,882 A | 6/1998 | Fogarty et al. | |
| 5,769,884 A | 6/1998 | Solovay | |
| 5,782,903 A | 7/1998 | Wiktor | |
| 5,782,906 A | 7/1998 | Marshall et al. | |
| 5,824,040 A | 10/1998 | Cox et al. | |
| 5,824,055 A | 10/1998 | Spiridigliozzi et al. | |
| 5,827,321 A | 10/1998 | Roubin | |
| 5,843,170 A | 12/1998 | Ahn | |
| 5,855,600 A | 1/1999 | Alt | |
| 5,860,991 A | 1/1999 | Klein et al. | |
| 5,876,432 A | 3/1999 | Lau et al. | |
| 5,906,641 A | 5/1999 | Thompson et al. | |
| 5,921,994 A | 7/1999 | Andreas et al. | |
| 5,925,076 A | 7/1999 | Inoue | |
| 5,944,750 A | 8/1999 | Tanner et al. | |
| 5,948,018 A | 9/1999 | Dereume et al. | |
| 5,968,091 A | 10/1999 | Pinchuk et al. | |
| 5,972,017 A * | 10/1999 | Berg | A61F 2/06 128/898 |
| 5,976,178 A | 11/1999 | Goldsteen et al. | |
| 5,980,552 A | 11/1999 | Pinchasik | |
| 5,984,955 A | 11/1999 | Wisselink | |
| 6,015,431 A | 1/2000 | Thornton et al. | |
| 6,016,810 A | 1/2000 | Ravenscroft | |
| 6,030,414 A | 2/2000 | Taheri | |
| 6,033,435 A | 3/2000 | Penn et al. | |
| 6,036,723 A | 3/2000 | Anidjar et al. | |
| 6,036,725 A | 3/2000 | Avellanet | |
| 6,051,021 A | 4/2000 | Frid | |
| 6,059,824 A | 5/2000 | Taheri | |
| 6,077,298 A | 6/2000 | Tu et al. | |
| 6,099,497 A | 8/2000 | Adams et al. | |
| 6,099,548 A | 8/2000 | Taheri | |
| 6,117,145 A | 9/2000 | Wood et al. | |
| 6,129,738 A | 10/2000 | Lashinski et al. | |
| 6,132,457 A | 10/2000 | Chobotov | |
| 6,152,937 A * | 11/2000 | Peterson | A61B 17/11 606/153 |
| 6,152,956 A | 11/2000 | Pierce | |
| 6,156,064 A | 12/2000 | Chouinard | |
| 6,159,228 A | 12/2000 | Frid et al. | |
| 6,168,615 B1 | 1/2001 | Ken et al. | |
| 6,176,875 B1 | 1/2001 | Lenker et al. | |
| 6,179,878 B1 | 1/2001 | Duerig et al. | |
| 6,200,339 B1 | 3/2001 | Leschinsky et al. | |
| 6,206,893 B1 | 3/2001 | Klein et al. | |
| 6,270,524 B1 | 8/2001 | Kim | |
| 6,283,991 B1 | 9/2001 | Cox et al. | |
| 6,287,335 B1 | 9/2001 | Drasler et al. | |
| 6,290,720 B1 | 9/2001 | Khosravi et al. | |
| 6,296,661 B1 | 10/2001 | Davila et al. | |
| 6,312,458 B1 | 11/2001 | Golds | |
| 6,319,287 B1 | 11/2001 | Frimberger | |
| 6,325,819 B1 | 12/2001 | Pavcnik et al. | |
| 6,325,823 B1 | 12/2001 | Horzewski et al. | |
| 6,325,826 B1 * | 12/2001 | Vardi | A61F 2/82 623/1.15 |
| 6,344,056 B1 * | 2/2002 | Dehdashtian | A61F 2/07 623/1.35 |
| 6,395,018 B1 | 5/2002 | Castaneda | |
| 6,406,420 B1 | 6/2002 | McCarthy | |
| 6,428,565 B1 | 8/2002 | Wisselink | |
| 6,451,048 B1 | 9/2002 | Berg et al. | |
| 6,451,051 B2 | 9/2002 | Drasler et al. | |
| 6,471,722 B1 | 10/2002 | Inoue | |
| 6,506,211 B1 | 1/2003 | Skubitz et al. | |
| 6,520,988 B1 | 2/2003 | Colombo et al. | |
| 6,544,279 B1 | 4/2003 | Hopkins et al. | |
| 6,565,597 B1 | 5/2003 | Fearnot et al. | |
| 6,576,009 B2 | 6/2003 | Ryan et al. | |
| 6,613,075 B1 | 9/2003 | Healy et al. | |
| 6,613,078 B1 | 9/2003 | Barone | |
| 6,635,083 B1 | 10/2003 | Cheng et al. | |
| 6,645,242 B1 | 11/2003 | Quinn | |
| 6,648,901 B2 | 11/2003 | Fleischman et al. | |
| 6,648,911 B1 | 11/2003 | Sirhan | |
| 6,652,567 B1 | 11/2003 | Deaton | |
| 6,652,571 B1 | 11/2003 | White et al. | |
| 6,656,214 B1 | 12/2003 | Fogarty et al. | |
| 6,673,080 B2 | 1/2004 | Reynolds et al. | |
| 6,692,520 B1 | 2/2004 | Gambale et al. | |
| 6,695,833 B1 | 2/2004 | Frantzen | |
| 6,695,875 B2 | 2/2004 | Stelter et al. | |
| 6,699,277 B1 | 3/2004 | Freidberg et al. | |
| 6,716,238 B2 | 4/2004 | Elliot | |

(56) References Cited

U.S. PATENT DOCUMENTS

| | | | |
|---|---|---|---|
| 6,729,356 B1 | 5/2004 | Baker et al. |
| 6,730,117 B1 | 5/2004 | Tseng et al. |
| 6,733,523 B2 | 5/2004 | Shaolian et al. |
| 6,743,195 B2 | 6/2004 | Zucker |
| 6,748,953 B2 | 6/2004 | Sherry et al. |
| 6,752,826 B2 | 6/2004 | Wholey et al. |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,843,803 B2 | 1/2005 | Ryan et al. |
| 6,846,321 B2 | 1/2005 | Zucker |
| 6,860,900 B2 | 3/2005 | Clerc et al. |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,953,469 B2 | 10/2005 | Ryan |
| 6,964,679 B1 | 11/2005 | Marcade et al. |
| 6,986,774 B2 | 1/2006 | Middleman et al. |
| 7,008,441 B2 | 3/2006 | Zucker |
| 7,018,400 B2 | 3/2006 | Lashinski et al. |
| 7,022,131 B1 | 4/2006 | DeRowe et al. |
| 7,044,962 B2 | 5/2006 | Elliott |
| 7,083,822 B2 | 8/2006 | Brightbill |
| 7,105,015 B2 | 9/2006 | Goshgarian |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,122,052 B2 | 10/2006 | Greenhalgh |
| 7,131,991 B2 | 11/2006 | Zarins et al. |
| 7,144,421 B2 | 12/2006 | Carpenter et al. |
| 7,160,318 B2 | 1/2007 | Greenberg et al. |
| 7,175,651 B2 | 2/2007 | Kerr |
| 7,198,638 B2 | 4/2007 | Dong |
| 7,201,772 B2 | 4/2007 | Schwammenthal et al. |
| 7,220,274 B1 | 5/2007 | Quinn |
| 7,223,266 B2 | 5/2007 | Lindenbaum et al. |
| 7,261,733 B1 | 8/2007 | Brown et al. |
| 7,270,675 B2 | 9/2007 | Chun et al. |
| 7,279,003 B2 | 10/2007 | Berra et al. |
| 7,294,145 B2 | 11/2007 | Ward |
| 7,294,147 B2 | 11/2007 | Hartley |
| 7,306,623 B2 | 12/2007 | Watson |
| 7,341,598 B2 | 3/2008 | Davidson et al. |
| 7,393,357 B2 | 7/2008 | Stelter et al. |
| 7,396,363 B2 | 7/2008 | Frid |
| 7,399,313 B2 | 7/2008 | Brown et al. |
| 7,407,509 B2 * | 8/2008 | Greenberg | A61F 2/07 606/153 |
| 7,413,573 B2 | 8/2008 | Hartley et al. |
| 7,425,219 B2 | 9/2008 | Quadri |
| 7,429,269 B2 | 9/2008 | Schwammenthal et al. |
| 7,438,721 B2 | 10/2008 | Doig et al. |
| 7,442,204 B2 | 10/2008 | Schwammenthal et al. |
| 7,473,272 B2 | 1/2009 | Pryor |
| 7,491,231 B2 | 2/2009 | Nazzaro et al. |
| 7,537,606 B2 | 5/2009 | Hartley et al. |
| 7,537,609 B2 | 5/2009 | Davidson et al. |
| 7,540,881 B2 | 6/2009 | Meyer et al. |
| 7,544,160 B2 | 6/2009 | Gross |
| 7,575,590 B2 | 8/2009 | Watson |
| 7,616,997 B2 | 11/2009 | Kieval et al. |
| 7,637,939 B2 | 12/2009 | Tischler |
| 7,645,298 B2 | 1/2010 | Hartley et al. |
| 7,662,161 B2 | 2/2010 | Briganti et al. |
| 7,662,168 B2 | 2/2010 | McGuckin, Jr. et al. |
| 7,670,369 B2 | 3/2010 | Schaeffer |
| 7,678,141 B2 * | 3/2010 | Greenan | A61F 2/07 623/1.13 |
| 7,699,885 B2 | 4/2010 | Leonhardt et al. |
| 7,708,704 B2 | 5/2010 | Mitelberg |
| 7,722,626 B2 | 5/2010 | Middleman et al. |
| 7,731,732 B2 | 6/2010 | Ken |
| 7,731,741 B2 * | 6/2010 | Eidenschink | A61F 2/07 623/1.11 |
| 7,766,955 B2 | 8/2010 | Vardi et al. |
| 7,771,465 B2 | 8/2010 | Zukowski |
| 7,789,903 B2 | 9/2010 | Spiridigliozzi et al. |
| 7,803,177 B2 | 9/2010 | Hartley et al. |
| 7,803,178 B2 | 9/2010 | Whirley |
| 7,806,923 B2 | 10/2010 | Moloney |
| 7,815,673 B2 | 10/2010 | Bloom et al. |
| 7,833,259 B2 | 11/2010 | Boatman |
| 7,833,264 B2 * | 11/2010 | Hegg | A61F 2/856 623/1.15 |
| 7,833,266 B2 * | 11/2010 | Gregorich | A61F 2/856 623/1.35 |
| 7,842,081 B2 * | 11/2010 | Yadin | A61F 2/856 623/1.15 |
| 7,846,194 B2 | 12/2010 | Hartley et al. |
| 7,850,725 B2 | 12/2010 | Vardi et al. |
| 7,867,270 B2 | 1/2011 | Hartley et al. |
| 7,887,575 B2 | 2/2011 | Kujawski |
| 7,914,572 B2 | 3/2011 | Hartley et al. |
| 7,955,373 B2 | 6/2011 | Sowinski et al. |
| 7,955,374 B2 | 6/2011 | Erickson et al. |
| 7,959,662 B2 | 6/2011 | Erbel et al. |
| 7,959,668 B2 * | 6/2011 | Yadin | A61F 2/856 623/1.15 |
| 7,959,669 B2 | 6/2011 | Chalekian et al. |
| 7,998,186 B2 | 8/2011 | Hartley |
| 7,998,187 B2 | 8/2011 | Hartley et al. |
| 8,012,193 B2 | 9/2011 | Hartley et al. |
| 8,016,853 B2 | 9/2011 | Griffen et al. |
| 8,021,412 B2 | 9/2011 | Hartley et al. |
| 8,021,418 B2 | 9/2011 | Gerberding et al. |
| 8,021,419 B2 | 9/2011 | Hartley et al. |
| 8,043,365 B2 | 10/2011 | Thramann |
| 8,048,139 B2 | 11/2011 | Frid et al. |
| 8,048,140 B2 | 11/2011 | Purdy |
| 8,048,147 B2 | 11/2011 | Adams |
| 8,052,736 B2 | 11/2011 | Doig et al. |
| 8,052,741 B2 | 11/2011 | Bruszewski et al. |
| 8,066,755 B2 | 11/2011 | Zacharias |
| 8,080,026 B2 | 12/2011 | Konstantino et al. |
| 8,080,053 B2 | 12/2011 | Satasiya |
| 8,100,960 B2 | 1/2012 | Bruszewski |
| 8,118,854 B2 | 2/2012 | Bowe |
| 8,133,267 B2 | 3/2012 | Leonhardt et al. |
| 8,157,810 B2 | 4/2012 | Case et al. |
| 8,167,926 B2 | 5/2012 | Hartley et al. |
| 8,172,892 B2 | 5/2012 | Chuter |
| 8,172,895 B2 | 5/2012 | Anderson et al. |
| 8,197,475 B2 | 6/2012 | Bruszewski et al. |
| 8,197,533 B2 | 6/2012 | Kujawski |
| 8,211,158 B2 | 7/2012 | Wolf |
| 8,216,298 B2 | 7/2012 | Wright et al. |
| 8,221,494 B2 | 7/2012 | Schreck et al. |
| 8,226,706 B2 | 7/2012 | Hartley et al. |
| 8,236,040 B2 | 8/2012 | Mayberry et al. |
| 8,251,963 B2 | 8/2012 | Chin et al. |
| 8,257,423 B2 | 9/2012 | Kerr |
| 8,262,719 B2 | 9/2012 | Erickson et al. |
| 8,273,115 B2 | 9/2012 | Hamer et al. |
| 8,277,501 B2 * | 10/2012 | Chalekian | A61F 2/856 623/1.15 |
| 8,287,586 B2 | 10/2012 | Schaeffer et al. |
| 8,292,885 B2 | 10/2012 | Bruszewski et al. |
| 8,292,941 B2 | 10/2012 | Muzslay |
| 8,292,949 B2 | 10/2012 | Berra et al. |
| 8,292,951 B2 | 10/2012 | Muzslay |
| 8,333,800 B2 | 12/2012 | Bruszewski et al. |
| 8,337,546 B2 | 12/2012 | Bruszewski |
| 8,353,898 B2 | 1/2013 | Lutze et al. |
| 8,357,192 B2 | 1/2013 | Mayberry et al. |
| 8,361,134 B2 | 1/2013 | Hartley et al. |
| 8,394,136 B2 | 3/2013 | Hartley et al. |
| 8,425,585 B2 | 4/2013 | Melsheimer et al. |
| 8,470,018 B2 | 6/2013 | Hartley et al. |
| 8,475,513 B2 | 7/2013 | Sithian |
| 8,480,726 B2 | 7/2013 | Cunningham et al. |
| 8,486,131 B2 | 7/2013 | Shalev |

(56) References Cited

U.S. PATENT DOCUMENTS

| | | |
|---|---|---|
| 8,491,646 B2 | 7/2013 | Schreck |
| 8,506,622 B2 | 8/2013 | Bruszewski et al. |
| 8,728,148 B2 | 5/2014 | Roeder et al. |
| 8,808,355 B2 | 8/2014 | Barrand |
| 8,945,203 B2 | 2/2015 | Shalev et al. |
| 8,968,384 B2 | 3/2015 | Pearson et al. |
| 9,101,457 B2 | 8/2015 | Benary |
| 9,168,123 B2 | 10/2015 | Barrand |
| 9,254,209 B2 | 2/2016 | Shalev |
| 9,597,204 B2 | 3/2017 | Benary et al. |
| 2001/0000188 A1 | 4/2001 | Lenker et al. |
| 2001/0003161 A1 | 6/2001 | Vardi et al. |
| 2001/0004705 A1 | 6/2001 | Killion |
| 2001/0010006 A1 | 7/2001 | Bachinski et al. |
| 2001/0014823 A1 | 8/2001 | Resseman et al. |
| 2001/0034550 A1 | 10/2001 | Buirge |
| 2001/0037142 A1 | 11/2001 | Stelter et al. |
| 2001/0044647 A1 | 11/2001 | Pinchuk et al. |
| 2001/0044651 A1 | 11/2001 | Steinke |
| 2001/0044652 A1 | 11/2001 | Moore |
| 2001/0047198 A1 | 11/2001 | Drasler |
| 2001/0049550 A1 | 12/2001 | Martin et al. |
| 2001/0053930 A1 | 12/2001 | Kugler et al. |
| 2002/0040236 A1 | 4/2002 | Lau |
| 2002/0052643 A1 | 5/2002 | Wholey et al. |
| 2002/0052644 A1 | 5/2002 | Shaolian et al. |
| 2002/0072790 A1* | 6/2002 | McGuckin, Jr. ......... A61F 2/07 623/1.12 |
| 2002/0099438 A1 | 7/2002 | Furst |
| 2002/0099441 A1 | 7/2002 | Dehdashtian |
| 2002/0107564 A1 | 8/2002 | Cox |
| 2002/0111667 A1 | 8/2002 | Girton et al. |
| 2002/0123791 A1 | 9/2002 | Harrison |
| 2002/0156495 A1 | 10/2002 | Brenneman et al. |
| 2002/0156517 A1 | 10/2002 | Prouse et al. |
| 2002/0173809 A1 | 11/2002 | Fleischman et al. |
| 2002/0173840 A1* | 11/2002 | Brucker ................ A61F 2/95 623/1.16 |
| 2002/0183783 A1 | 12/2002 | Shadduck |
| 2002/0193864 A1 | 12/2002 | Khosravi et al. |
| 2002/0198585 A1 | 12/2002 | Wisselink |
| 2003/0033005 A1 | 2/2003 | Houser et al. |
| 2003/0040791 A1 | 2/2003 | Oktay |
| 2003/0040804 A1 | 2/2003 | Stack et al. |
| 2003/0057156 A1 | 3/2003 | Peterson et al. |
| 2003/0065345 A1 | 4/2003 | Weadock |
| 2003/0065386 A1 | 4/2003 | Weadock |
| 2003/0074055 A1 | 4/2003 | Haverkost |
| 2003/0093145 A1 | 5/2003 | Lawrence-Brown et al. |
| 2003/0114061 A1 | 6/2003 | Matsuda et al. |
| 2003/0125796 A1 | 7/2003 | Dong |
| 2003/0130720 A1 | 7/2003 | DePalma et al. |
| 2003/0139802 A1 | 7/2003 | Wulfman et al. |
| 2003/0139805 A1 | 7/2003 | Holmberg et al. |
| 2003/0144725 A1 | 7/2003 | Lombardi |
| 2003/0153944 A1 | 8/2003 | Phung et al. |
| 2003/0153968 A1 | 8/2003 | Geis et al. |
| 2003/0163187 A1 | 8/2003 | Weber |
| 2003/0171771 A1 | 9/2003 | Anderson et al. |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0204236 A1 | 10/2003 | Letort |
| 2003/0204242 A1 | 10/2003 | Zarins et al. |
| 2003/0204243 A1 | 10/2003 | Shiu |
| 2003/0208192 A1 | 11/2003 | Truckai et al. |
| 2003/0212449 A1 | 11/2003 | Cox |
| 2003/0233117 A1 | 12/2003 | Adams et al. |
| 2003/0236567 A1 | 12/2003 | Elliot |
| 2004/0015227 A1 | 1/2004 | Vardi et al. |
| 2004/0015229 A1 | 1/2004 | Fulkerson |
| 2004/0098091 A1 | 5/2004 | Erbel |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0138735 A1 | 7/2004 | Shaolian et al. |
| 2004/0162606 A1 | 8/2004 | Thompson |
| 2004/0171978 A1 | 9/2004 | Shalaby |
| 2004/0176832 A1 | 9/2004 | Hartley et al. |
| 2004/0181149 A1 | 9/2004 | Langlotz et al. |
| 2004/0215319 A1 | 10/2004 | Berra et al. |
| 2004/0215320 A1 | 10/2004 | MacHek |
| 2004/0215327 A1 | 10/2004 | Doig et al. |
| 2004/0215332 A1 | 10/2004 | Frid |
| 2004/0260383 A1 | 12/2004 | Stelter et al. |
| 2005/0010246 A1 | 1/2005 | Streeter et al. |
| 2005/0033406 A1 | 2/2005 | Barnhart et al. |
| 2005/0049678 A1 | 3/2005 | Cocks et al. |
| 2005/0059923 A1 | 3/2005 | Gamboa |
| 2005/0065545 A1 | 3/2005 | Wallace |
| 2005/0070995 A1 | 3/2005 | Zilla et al. |
| 2005/0085900 A1 | 4/2005 | Case |
| 2005/0102018 A1 | 5/2005 | Carpenter et al. |
| 2005/0102021 A1 | 5/2005 | Osborne |
| 2005/0131512 A1 | 6/2005 | Vonderwalde |
| 2005/0131517 A1 | 6/2005 | Hartley et al. |
| 2005/0137682 A1 | 6/2005 | Justino |
| 2005/0143802 A1 | 6/2005 | Soykan et al. |
| 2005/0149166 A1 | 7/2005 | Schaeffer et al. |
| 2005/0154448 A1 | 7/2005 | Cully |
| 2005/0159803 A1 | 7/2005 | Lad et al. |
| 2005/0165480 A1 | 7/2005 | Jordan et al. |
| 2005/0171598 A1 | 8/2005 | Schaeffer et al. |
| 2005/0171599 A1 | 8/2005 | White |
| 2005/0177132 A1 | 8/2005 | Lentz et al. |
| 2005/0177222 A1 | 8/2005 | Mead |
| 2005/0177224 A1 | 8/2005 | Fogarty et al. |
| 2005/0203606 A1 | 9/2005 | VanCamp |
| 2005/0216018 A1 | 9/2005 | Sennett et al. |
| 2005/0222649 A1 | 10/2005 | Capuano |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0228480 A1 | 10/2005 | Douglas et al. |
| 2005/0234542 A1 | 10/2005 | Melsheimer |
| 2005/0266042 A1 | 12/2005 | Tseng |
| 2005/0273155 A1 | 12/2005 | Bahler et al. |
| 2005/0283188 A1 | 12/2005 | Loshakove et al. |
| 2006/0015170 A1 | 1/2006 | Jones et al. |
| 2006/0030911 A1 | 2/2006 | Letort |
| 2006/0030921 A1 | 2/2006 | Chu |
| 2006/0052799 A1 | 3/2006 | Middleman et al. |
| 2006/0069426 A1 | 3/2006 | Weinberger |
| 2006/0095104 A1 | 5/2006 | Magers et al. |
| 2006/0095114 A1 | 5/2006 | Hartley et al. |
| 2006/0100684 A1 | 5/2006 | Elliott |
| 2006/0106406 A1 | 5/2006 | Weinberger |
| 2006/0116748 A1 | 6/2006 | Kaplan et al. |
| 2006/0149360 A1 | 7/2006 | Schwammenthal et al. |
| 2006/0155358 A1 | 7/2006 | LaDuca et al. |
| 2006/0155359 A1 | 7/2006 | Watson |
| 2006/0155362 A1* | 7/2006 | Israel .................... A61F 2/856 623/1.15 |
| 2006/0155366 A1 | 7/2006 | LaDuca et al. |
| 2006/0167476 A1 | 7/2006 | Burdulis, Jr. et al. |
| 2006/0173528 A1* | 8/2006 | Feld .................... A61F 2/856 623/1.15 |
| 2006/0173530 A1 | 8/2006 | Das |
| 2006/0178733 A1 | 8/2006 | Pinchuk et al. |
| 2006/0190070 A1 | 8/2006 | Dieck et al. |
| 2006/0193892 A1 | 8/2006 | Furst et al. |
| 2006/0212113 A1 | 9/2006 | Shaolian et al. |
| 2006/0229709 A1 | 10/2006 | Morris et al. |
| 2006/0241740 A1 | 10/2006 | Vardi et al. |
| 2006/0271166 A1 | 11/2006 | Thill et al. |
| 2006/0276882 A1 | 12/2006 | Case et al. |
| 2006/0281966 A1 | 12/2006 | Peacock, III |
| 2006/1010640 | 12/2006 | Peacock, III |
| 2007/0016281 A1 | 1/2007 | Melsheimer |
| 2007/0021822 A1 | 1/2007 | Boatman |
| 2007/0027526 A1 | 2/2007 | Demetriades et al. |
| 2007/0043425 A1 | 2/2007 | Hartley et al. |
| 2007/0050011 A1 | 3/2007 | Klein |

(56) References Cited

U.S. PATENT DOCUMENTS

| | | |
|---|---|---|
| 2007/0055326 A1 | 3/2007 | Farley et al. |
| 2007/0055350 A1 | 3/2007 | Erickson et al. |
| 2007/0055358 A1 | 3/2007 | Krolik et al. |
| 2007/0055360 A1 | 3/2007 | Hanson et al. |
| 2007/0060989 A1 | 3/2007 | Deem et al. |
| 2007/0061002 A1 | 3/2007 | Paul, Jr. |
| 2007/0067014 A1 | 3/2007 | Ke et al. |
| 2007/0073373 A1 | 3/2007 | Bonsignore |
| 2007/0088425 A1 | 4/2007 | Schaeffer |
| 2007/0106368 A1 | 5/2007 | Vonderwalde |
| 2007/0112344 A1 | 5/2007 | Keilman |
| 2007/0135677 A1 | 6/2007 | Miller et al. |
| 2007/0135904 A1 | 6/2007 | Eidenschink et al. |
| 2007/0142896 A1 | 6/2007 | Anderson et al. |
| 2007/0150051 A1 | 6/2007 | Arnault de la et al. |
| 2007/0156167 A1 | 7/2007 | Connors et al. |
| 2007/0162104 A1 | 7/2007 | Frid |
| 2007/0167898 A1 | 7/2007 | Peters et al. |
| 2007/0167955 A1 | 7/2007 | Arnault De La Menardiere et al. |
| 2007/0168013 A1 | 7/2007 | Douglas |
| 2007/0168018 A1 | 7/2007 | Amplatz |
| 2007/0179598 A1 | 8/2007 | Duerig |
| 2007/0185565 A1 | 8/2007 | Schwammenthal et al. |
| 2007/0207186 A1 | 9/2007 | Scanlon et al. |
| 2007/0208410 A1 | 9/2007 | Berra et al. |
| 2007/0208419 A1* | 9/2007 | Meyer ................ A61F 2/856 623/1.35 |
| 2007/0213805 A1 | 9/2007 | Schaeffer et al. |
| 2007/0213807 A1 | 9/2007 | Roubin |
| 2007/0219610 A1 | 9/2007 | Israel |
| 2007/0219614 A1 | 9/2007 | Hartley |
| 2007/0219627 A1 | 9/2007 | Chu |
| 2007/0225797 A1 | 9/2007 | Krivoruhko |
| 2007/0233229 A1 | 10/2007 | Berra et al. |
| 2007/0237973 A1 | 10/2007 | Purdy et al. |
| 2007/0239256 A1 | 10/2007 | Weber et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0015682 A1 | 1/2008 | Majercak et al. |
| 2008/0033527 A1 | 2/2008 | Nunez et al. |
| 2008/0058918 A1 | 3/2008 | Watson |
| 2008/0064957 A1 | 3/2008 | Spence |
| 2008/0086193 A1 | 4/2008 | Thramann |
| 2008/0097578 A1 | 4/2008 | Erickson et al. |
| 2008/0109058 A1 | 5/2008 | Greenberg et al. |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0114446 A1 | 5/2008 | Hartley et al. |
| 2008/0140178 A1 | 6/2008 | Rasmussen et al. |
| 2008/0147173 A1 | 6/2008 | McIff et al. |
| 2008/0167704 A1 | 7/2008 | Wright et al. |
| 2008/0176271 A1 | 7/2008 | Silver et al. |
| 2008/0195190 A1 | 8/2008 | Bland et al. |
| 2008/0195191 A1 | 8/2008 | Luo |
| 2008/0215134 A1 | 9/2008 | Lawrence-Brown |
| 2008/0249598 A1 | 10/2008 | Sherry |
| 2008/0262595 A1 | 10/2008 | Chu et al. |
| 2008/0262598 A1 | 10/2008 | Elmaleh |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz |
| 2008/0312732 A1 | 12/2008 | Hartley et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang |
| 2009/0069881 A1 | 3/2009 | Chalekian et al. |
| 2009/0069882 A1 | 3/2009 | Venturelli |
| 2009/0082841 A1 | 3/2009 | Zacharias |
| 2009/0082847 A1 | 3/2009 | Zacharias et al. |
| 2009/0099640 A1 | 4/2009 | Weng |
| 2009/0099647 A1 | 4/2009 | Glimsdale et al. |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0157014 A1 | 6/2009 | Osborne et al. |
| 2009/0163993 A1* | 6/2009 | Chalekian ................ A61F 2/856 623/1.15 |
| 2009/0164001 A1 | 6/2009 | Biggs et al. |
| 2009/0171437 A1* | 7/2009 | Brocker ................... A61F 2/07 623/1.13 |
| 2009/0182270 A1 | 7/2009 | Nanavati |
| 2009/0182405 A1 | 7/2009 | Arnault De La Menardiere et al. |
| 2009/0192587 A1 | 7/2009 | Frid |
| 2009/0227997 A1 | 9/2009 | Wang |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2009/0319022 A1 | 12/2009 | Hartley et al. |
| 2010/0004728 A1 | 1/2010 | Rao |
| 2010/0029608 A1 | 2/2010 | Finley |
| 2010/0057186 A1 | 3/2010 | West et al. |
| 2010/0063575 A1 | 3/2010 | Shalev |
| 2010/0070019 A1 | 3/2010 | Shalev |
| 2010/0082091 A1 | 4/2010 | Berez |
| 2010/0161025 A1 | 6/2010 | Kuppurathanam et al. |
| 2010/0161026 A1 | 6/2010 | Brocker et al. |
| 2010/0161028 A1 | 6/2010 | Chuter et al. |
| 2010/0168838 A1 | 7/2010 | Hartley et al. |
| 2010/0211159 A1 | 8/2010 | Schmid |
| 2010/0249899 A1 | 9/2010 | Chuter et al. |
| 2010/0256725 A1 | 10/2010 | Rasmussen |
| 2010/0262227 A1 | 10/2010 | Rangwala et al. |
| 2010/0268327 A1 | 10/2010 | Bruszewski et al. |
| 2010/0274187 A1 | 10/2010 | Argentine |
| 2010/0274345 A1 | 10/2010 | Rust |
| 2010/0292774 A1 | 11/2010 | Shalev |
| 2010/0312326 A1 | 12/2010 | Chuter et al. |
| 2010/0318171 A1 | 12/2010 | Porter |
| 2010/0318180 A1 | 12/2010 | Porter |
| 2011/0022149 A1 | 1/2011 | Cox et al. |
| 2011/0022153 A1 | 1/2011 | Schreck et al. |
| 2011/0040366 A1 | 2/2011 | Goetz et al. |
| 2011/0093002 A1 | 4/2011 | Rucker et al. |
| 2011/0125251 A1 | 5/2011 | Cottone |
| 2011/0152998 A1 | 6/2011 | Berez et al. |
| 2011/0208289 A1* | 8/2011 | Shalev ................... A61F 2/07 623/1.15 |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0218609 A1 | 9/2011 | Chobotov et al. |
| 2011/0218617 A1 | 9/2011 | Nguyen et al. |
| 2011/0319983 A1 | 9/2011 | Zhu et al. |
| 2011/0257720 A1 | 10/2011 | Peterson et al. |
| 2011/0257725 A1 | 10/2011 | Argentine et al. |
| 2011/0262684 A1 | 10/2011 | Wintsch et al. |
| 2011/0264184 A1 | 10/2011 | Heltai |
| 2011/0264192 A1 | 10/2011 | Hartley et al. |
| 2011/0270380 A1* | 11/2011 | Bruszewski ............... A61F 2/07 623/1.15 |
| 2011/0270385 A1 | 11/2011 | Muzslay |
| 2011/0288622 A1 | 11/2011 | Chan et al. |

(56) References Cited

U.S. PATENT DOCUMENTS

| | | |
|---|---|---|
| 2011/0301702 A1 | 12/2011 | Rust et al. |
| 2012/0143317 A1 | 6/2012 | Cam et al. |
| 2012/0150274 A1 | 6/2012 | Shalev et al. |
| 2012/0158038 A1 | 6/2012 | Leschinsky |
| 2012/0172929 A1 | 7/2012 | Shalev |
| 2012/0172965 A1 | 7/2012 | Kratzberg et al. |
| 2012/0179236 A1 | 7/2012 | Benary |
| 2012/0185031 A1 | 7/2012 | Ryan et al. |
| 2012/0271401 A1 | 10/2012 | Bruszewski et al. |
| 2012/0310324 A1 | 12/2012 | Benary et al. |
| 2012/0316634 A1 | 12/2012 | Shalev et al. |
| 2012/0323305 A1 | 12/2012 | Benary et al. |
| 2012/0330399 A1 | 12/2012 | Shalev et al. |
| 2013/0013050 A1 | 1/2013 | Shalev et al. |
| 2013/0013051 A1 | 1/2013 | Benary |
| 2013/0035751 A1 | 2/2013 | Shalev |
| 2013/0090722 A1 | 4/2013 | Shalev et al. |
| 2013/0116773 A1 | 5/2013 | Roeder et al. |
| 2013/0116775 A1 | 5/2013 | Roeder et al. |
| 2013/0131783 A1 | 5/2013 | Shalev et al. |
| 2013/0158646 A1 | 6/2013 | Roeder |
| 2013/0197454 A1 | 8/2013 | Shibata et al. |
| 2013/0204311 A1 | 8/2013 | Kunis |
| 2013/0204343 A1 | 8/2013 | Shalev |
| 2013/0261994 A1 | 10/2013 | Raz et al. |
| 2013/0274866 A1 | 10/2013 | Cox et al. |
| 2013/0289587 A1 | 10/2013 | Shalev |
| 2013/0297005 A1 | 11/2013 | Shalev |
| 2013/0338753 A1 | 12/2013 | Geusen |
| 2014/0005764 A1 | 1/2014 | Schroeder |
| 2014/0052236 A1 | 2/2014 | Shalev |
| 2014/0148888 A1 | 5/2014 | Barrand |
| 2014/0172072 A1 | 6/2014 | Shalev |
| 2014/0180378 A1 | 6/2014 | Roeder |
| 2014/0288634 A1 | 9/2014 | Shalev |
| 2014/0288635 A1 | 9/2014 | Shalev |
| 2014/0316510 A1 | 10/2014 | Berra |
| 2014/0324154 A1 | 10/2014 | Shalev |
| 2014/0350658 A1 | 11/2014 | Benary et al. |
| 2014/0364930 A1 | 12/2014 | Strauss et al. |
| 2015/0073534 A1 | 3/2015 | Roeder et al. |
| 2015/0105851 A1 | 4/2015 | Shalev et al. |
| 2015/0142096 A1 | 5/2015 | Shalev |
| 2015/0196301 A1 | 7/2015 | Bodewadt et al. |
| 2015/0202065 A1 | 7/2015 | Shalev et al. |
| 2015/0351943 A1 | 12/2015 | Shalev et al. |
| 2015/0374383 A1 | 12/2015 | Bodewadt et al. |
| 2016/0030209 A1 | 2/2016 | Shalev et al. |
| 2016/0157990 A1 | 6/2016 | Shalev et al. |
| 2016/0193029 A1 | 7/2016 | Shalev |
| 2016/0262880 A1 | 9/2016 | Li et al. |
| 2016/0302950 A1 | 10/2016 | Marmur et al. |

FOREIGN PATENT DOCUMENTS

| | | |
|---|---|---|
| CN | 2453960 | 10/2001 |
| CN | 1748660 | 3/2006 |
| CN | 2817770 | 9/2006 |
| CN | 101045022 | 10/2007 |
| CN | 201058061 | 5/2008 |
| CN | 101980670 | 2/2011 |
| CN | 101998845 | 3/2011 |
| DE | 10213055 | 9/2002 |
| EP | 0893108 | 1/1999 |
| EP | 1 177 779 | 2/2002 |
| EP | 1 177 780 | 2/2002 |
| EP | 1 325 716 | 7/2003 |
| EP | 1470797 | 10/2004 |
| EP | 1759666 | 3/2007 |
| EP | 1961401 | 8/2008 |
| EP | 2266509 | 12/2010 |
| EP | 2298248 | 3/2011 |
| EP | 2702964 | 3/2014 |
| JP | 2000-279533 | 10/2000 |
| JP | 2002-253682 | 9/2002 |
| WO | 1996/039104 | 12/1996 |
| WO | 98/06355 | 2/1998 |
| WO | 1998/027895 | 7/1998 |
| WO | 99/13808 | 3/1999 |
| WO | 1999/025273 | 5/1999 |
| WO | 99/34748 | 7/1999 |
| WO | 1999/051165 | 10/1999 |
| WO | 00/28923 | 5/2000 |
| WO | 2000/074595 | 12/2000 |
| WO | 2000/076423 | 12/2000 |
| WO | 2002/083038 | 10/2002 |
| WO | 2003/034948 | 5/2003 |
| WO | 03/099108 | 12/2003 |
| WO | 2004/017868 | 3/2004 |
| WO | 2004/045463 | 6/2004 |
| WO | 2004/100836 | 11/2004 |
| WO | 05/002466 | 1/2005 |
| WO | 2005/034809 | 4/2005 |
| WO | 2005/037138 | 4/2005 |
| WO | 2005/041781 | 5/2005 |
| WO | 2005/041783 | 5/2005 |
| WO | 2005/046524 | 5/2005 |
| WO | 2005/046526 | 5/2005 |
| WO | 2006/007389 | 1/2006 |
| WO | 2006/028925 | 3/2006 |
| WO | 2006/036690 | 4/2006 |
| WO | 06/070372 | 7/2006 |
| WO | 2006/088905 | 8/2006 |
| WO | 2006/130755 | 12/2006 |
| WO | 2007/022495 | 2/2007 |
| WO | 2007/039587 | 4/2007 |
| WO | 2007/084547 | 7/2007 |
| WO | 2007/115017 | 10/2007 |
| WO | 2007/144782 | 12/2007 |
| WO | 08/008291 | 1/2008 |
| WO | 2008/021557 | 2/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/051704 | 5/2008 |
| WO | 2008/053469 | 5/2008 |
| WO | 2008/066923 | 6/2008 |
| WO | 2008/107885 | 9/2008 |
| WO | 2008/140796 | 11/2008 |
| WO | 2009/078010 | 6/2009 |
| WO | 2009/104000 | 8/2009 |
| WO | 2009/116041 | 9/2009 |
| WO | 2009/116042 | 9/2009 |
| WO | 09/118733 | 10/2009 |
| WO | 2010/024869 | 3/2010 |
| WO | 2010/024879 | 3/2010 |
| WO | 2010/027704 | 3/2010 |
| WO | 2010/031060 | 3/2010 |
| WO | 2010/042210 | 4/2010 |
| WO | 2010/045238 | 4/2010 |
| WO | 2010/062355 | 6/2010 |
| WO | 10/088776 | 8/2010 |
| WO | 2010/111583 | 9/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2001/052776 | 7/2011 |
| WO | 2011/080738 | 7/2011 |
| WO | 2011/095979 | 8/2011 |
| WO | 2011/100290 | 8/2011 |
| WO | 2011/106532 | 9/2011 |
| WO | 2011/106533 | 9/2011 |
| WO | 2011/106544 | 9/2011 |
| WO | 2011/116307 | 9/2011 |
| WO | 2011/136930 | 11/2011 |
| WO | 2012/039748 | 3/2012 |
| WO | 2012/049679 | 4/2012 |
| WO | 2012/104842 | 8/2012 |

(56) References Cited

FOREIGN PATENT DOCUMENTS

| WO | 2012/111006 | 8/2012 |
|---|---|---|
| WO | 2012/117395 | 9/2012 |
| WO | 2012/176187 | 12/2012 |
| WO | 2013/005207 | 1/2013 |
| WO | 2013/030818 | 3/2013 |
| WO | 2013/030819 | 3/2013 |
| WO | 2013/065040 | 5/2013 |
| WO | 2013/084235 | 6/2013 |
| WO | 2013/171730 | 11/2013 |
| WO | 2014/020609 | 2/2014 |
| WO | 2014/108895 | 7/2014 |
| WO | 2014/141232 | 9/2014 |
| WO | 2014/188412 | 11/2014 |
| WO | 2016/098113 | 6/2016 |
| WO | 2016/113731 | 7/2016 |
| WO | 2016/125137 | 8/2016 |
| WO | 2017/081679 | 5/2017 |

OTHER PUBLICATIONS

Fonseca A et al., "Intravascular ultrasound assessment of the novel AngioSculpt scoring balloon catheter for the treatment of complex coronary lesions," J Invasive Cardiol 20(1):21-7 (Jan. 2008).
Khlif H et al., "Contribution to the Improvement of Textile Vascular Prostheses Crimping," Trends in Applied Sciences Research 6(9):1019-1027 (2011).
An International Search Report dated Sep. 29, 2008, which issued during the prosecution of Applicant's PCT/IL08/000287.
A Written Opinion dated Sep. 29, 2008, which issued during the prosecution of Applicant's PCT/IL08/000287.
An International Search Report & Written Opinion both dated Nov. 26, 2013, which issued during the prosecution of Applicant's PCT/IL2013/050656.
An International Search Report dated Feb. 4, 2011, which issued during the prosecution of Applicant's PCT/IB2010/052861.
A Written Opinion dated Feb. 4, 2011, which issued during the prosecution of Applicant's PCT/IB2010/052861.
An International Search Report dated Dec. 3, 2010, which issued during the prosecution of Applicant's PCT/IL2010/000564.
A Written Opinion dated Dec. 3, 2010, which issued during the prosecution of Applicant's PCT/IL2010/000564.
An International Search Report dated Nov. 5, 2010, which issued during the prosecution of Applicant's PCT/IL2010/000549.
A Written Opinion dated Nov. 5, 2010, which issued during the prosecution of Applicant's PCT/IL2010/000549.
An International Search Report dated Oct. 6, 2011, which issued during the prosecution of Applicant's PCT/IL2010/000999.
An International Search Report dated Mar. 10, 2011, which issued during the prosecution of Applicant's PCT/IL2010/000917.
An International Search Report together with Written Opinion both dated Mar. 30, 2011, which issued during the prosecution of Applicant's PCT/IL2010/001018.
An International Search Report dated Apr. 18, 2011, which issued during the prosecution of Applicant's PCT/IL2010/001037.
An International Search Report dated May 23, 2011, which issued during the prosecution of Applicant's PCT/IL2010/001087.
An International Search Report dated Jun. 28, 2011, which issued during the prosecution of Applicant's PCT/IL2011/000135.
An International Search Report dated Jun. 30, 2009, which issued during the prosecution of Applicant's PCT/IL2008/001621.
A Written Opinion dated Jun. 30, 2009, which issued during the prosecution of Applicant's PCT/IL2008/001621.
An International Search Report dated Mar. 11, 2009, which issued during the prosecution of Applicant's PCT/IL2007/001312.
A Written Opinion dated Mar. 11, 2009, which issued during the prosecution of Applicant's PCT/IL2007/001312.
An English translation of an Office Action dated Aug. 25, 2011, which issued during the prosecution of Chinese Patent Application No. 200880014919.9.
An Office Action dated Nov. 12, 2010, which issued during the prosecution of U.S. Appl. No. 12/447,684.
An Office Action dated Apr. 27, 2011, which issued during the prosecution of U.S. Appl. No. 12/447,684.
An Office Action dated Feb. 25, 2013, which issued during the prosecution of U.S. Appl. No. 13/031,871.
An Office Action dated Feb. 27, 2013, which issued during the prosecution of U.S. Appl. No. 12/808,037.
An Extended European Search Report dated Dec. 13, 2012, which issued during the prosecution of Applicant's European App No. 08719912.1.
An International Search Report together with Written Opinion both dated Sep. 6, 2012, which issued during the prosecution of Applicant's PCT/IL2012/000190.
An International Search Report together with Written Opinion both dated Aug. 31, 2012, which issued during the prosecution of Applicant's PCT/IL2012/000148.
An Office Action dated Oct. 11, 2012, which issued during the prosecution of U.S. Appl. No. 13/031,871.
An Office Action dated Jun. 19, 2012, which issued during the prosecution of U.S. Appl. No. 12/808,037.
An International Search Report together with Written Opinion both dated Sep. 24, 2012, which issued during the prosecution of Applicant's PCT/IL2012/000060.
An International Search Report together with Written Opinion both dated Oct. 1, 2012, which issued during the prosecution of Applicant's PCT/IL2012/000241.
An International Search Report together with Written Opinion both dated Oct. 4, 2012, which issued during the prosecution of Applicant's PCT/IL2012/000269.
An International Search Report together with Written Opinion both dated Nov. 27, 201, which issued during the prosecution of Applicant's PCT/IL2012/000300.
An Office Action dated Jul. 22, 2016, which issued during the prosecution of Chinese Patent Application No. 201480012648.9.
An Office Action dated Oct. 28, 2011, which issued during the prosecution of U.S. Appl. No. 12/529,936.
An Office Action dated Mar. 24, 2011, which issued during the prosecution of U.S. Appl. No. 12/529,936.
An International Search Report and a Written Opinion both dated Jun. 14, 2013, which issued during the prosecution of Applicant's PCT/IL2012/050506.
Van Prehn J et al., "Oversizing of aortic stent grafts for abdominal aneurysm repair: a systematic review of the benefits and risks," Eur J Vase Endovase Surg. Jul. 2009;38(1):42-53. Epub May 9, 2009 (abstract only).
Fattori et al., Degenerative aneurysm of the descending aorta. Endovascular Treatment. pp. 1-11, 2007, European Association for Cardio-Thoracic Surgery.
An Office Action dated Jan. 12, 2016, which issued during the prosecution of U.S. Appl. No. 14/362,194.
European Search Report dated Aug. 31, 2016, which issued during the Prosecution of Applicant's European App No. 14762507.3.
An Office Action dated Feb. 5, 2015, which issued during the prosecution of U.S. Appl. No. 13/384,075.
An Office Action dated Feb. 23, 2015, which issued during the prosecution of U.S. Appl. No. 13/513,397.
European Search Report dated Feb. 26, 2015, which issued during the prosecution of Applicant's European App No. 12806964.8.
An International Search report and a Written Opinion both dated Mar. 18, 2015, which issued during the prosecution of Applicant's PCT/IL2014/050973.
An English translation of an Office Action dated Mar. 19, 2015, which issued Chinese Patent Application No. 201080036970.7.
An English translation of an Office Action dated Oct. 8, 2014, which issued during the prosecution of Chinese Patent Application No. 201080036970.7.
European Search Report dated May 23, 2016, which issued during the prosecution of Applicant's European App No. 10832752.9.
An Office Action dated Mar. 26, 2015, which issued during the prosecution of U.S. Appl. No. 13/514,240.
European Search Report dated Mar. 20, 2015, which issued during the prosecution of Applicant's European App No. 08861980.4.

(56) References Cited

OTHER PUBLICATIONS

An International Search Report and a Written Opinion both dated Jun. 21, 2016, which issued during the prosecution of Applicant's PCT/IL2016/050014.
An Office Action dated Aug. 12, 2015, which issued during the prosecution of U.S. Appl. No. 13/513,397.
European Search Report dated Sep. 22, 2016, which issued during the prosecution of Applicant's European App No. 10834308.8.
An Office Action dated Aug. 3, 2016, which issued during the prosecution of U.S. Appl. No. 14/241,793.
An Office Action dated Sep. 22, 2016, which issued during the prosecution of Canadian Patent Application No. 2,782,513.
An Office Action dated Sep. 23, 2015, which issued during the prosecution of U.S. Appl. No. 13/384,075.
An Office Action dated Oct. 2, 2015, which issued during the prosecution of U.S. Appl. No. 13/577,161.
European Search Report dated Apr. 22, 2015, which issued during the prosecution of Applicant's European App No. 12828495.7.
An Office Action dated Apr. 14, 2015, which issued during the prosecution of U.S. Appl. No. 14/130,213.
European Search Report dated Jan. 18, 2016 which issued during the prosecution of Applicant's European App No. 10799521.9.
European Search Report dated Oct. 27, 2015 which issued during the prosecution of Applicant's European App No. 10835608.0.
An Office Action dated Feb. 23, 2016, which issued during the prosecution of U.S. Appl. No. 14/416,236.
An Office Action dated Mar. 7, 2016, which issued during the prosecution of U.S. Appl. No. 14/240,600.
An Office Action dated Feb. 1, 2016, which issued during the prosecution of U.S. Appl. No. 14/241,793.
An Office Action dated Feb. 19, 2016, which issued during the prosecution of U.S. Appl. No. 13/807,880.
An International Search Report and a Written Opinion both dated Feb. 17, 2016, which issued during the prosecution of Applicant's PCT/IL2015/051221.
European Search Report dated Mar. 11, 2016 which issued during the prosecution of Applicant's European App No. 11739497.3.
European Search Report dated Mar. 15, 2016 which issued during the prosecution of Applicant's European App No. 13825456.0.
An Office Action dated Mar. 28, 2016, which issued during the prosecution of U.S. Appl. No. 14/362,194.
An Invitation to pay additional fees dated Apr. 12, 2016, which issued during the prosecution of Applicant's PCT/IL2016/050014.
An International Search Report and a Written Opinion both dated Apr. 22, 2016, which issued during the prosecution of Applicant's PCT/IL2016/050049.
Scurr et al., "Fenestrated Aortic Stent Grafts," Semin Intervent Radiol. Jun. 2007; 24(2): 211-220.
European Search Report dated Oct. 27, 2016 which issued during the prosecution of Applicant's European App No. 14801036.6.
U.S. Appl. No. 61/265,793, filed Dec. 2, 2009.
Notice of Allowance dated Dec. 30, 2015, which issued during the prosecution U.S. Appl. No. 14/130,213.
Notice of Allowance dated Oct. 16, 2015, which issued during the prosecution of U.S. Appl. No. 14/130,213.
Notice of Allowance dated Nov. 23, 2015, which issued during the prosecution of U.S. Appl. No. 14/130,213.
An Office Action dated Jan. 26, 2017, which issued during the prosecution of U.S. Appl. No. 14/572,156.
An Office Action dated Jul. 7, 2017, which issued during the prosecution of U.S. Appl. No. 14/572,156.
An Office Action dated Aug. 21, 2014, which issued during the prosecution of U.S. Appl. No. 13/384,075.
An Office Action dated Jun. 10, 2014, which issued during the prosecution of U.S. Appl. No. 13/505,996.
Notice of Allowance dated Nov. 10, 2016, which issued during the prosecution of U.S. Appl. No. 14/362,194.
An International Preliminary Report on Patentability dated Jun. 20, 2017, which issued during the prosecution of Applicant's PCT/IL2015/051221.

An Office Action dated Jul. 30, 2015, which issued during the prosecution of U.S. Appl. No. 14/240,600.
An Office Action dated May 28, 2015, which issued during the prosecution of U.S. Appl. No. 14/240,600.
An Office Action dated May 15, 2015, which issued during the prosecution of U.S. Appl. No. 13/577,161.
An Office Action dated Sep. 15, 2016, which issued during the prosecution of Canadian Patent Application No. 2,782,357.
An Office Action dated Mar. 28, 2014, which issued during the prosecution of U.S. Appl. No. 13/519,971.
U.S. Appl. No. 61/566,654, filed Dec. 4, 2011.
An International Search Report and a Written Opinion both dated Jul. 30, 2014, which issued during the prosecution of Applicant's PCT/IL2014/050174.
European Search Report dated Jun. 12, 2014, which issued during the prosecution of Applicant's European App No. 12855964.8.
European Office Action dated Dec. 17, 2014 in European Patent Application No. 12803376.8.
Supplementary European Search Report dated Feb. 17, 2014, which issued during the prosecution of Applicant's European App No. 12803376.8.
Invitation to Pay Additional Fees dated May 8, 2014, which issued during the prosecution of Applicant's PCT/IL2014/050174.
Invitation to Pay Additional Fees dated May 13, 2014, which issued during the prosecution of Applicant's PCT/IL2014/050019.
Aortic Aneurysm O'Gara, Patrick T. Circulation. 2003; 107:e43-e45.
An Office Action dated Jan. 12, 2017, which issued during the prosecution of U.S. Appl. No. 14/518,542.
An Office Action dated Dec. 7, 2016, which issued during the prosecution of U.S. Appl. No. 14/400,699.
An Office Action dated Dec. 27, 2016, which issued during the prosecution of Chinese Patent Application No. 201510685240.4.
An International Search Report and a Written Opinion both dated Jan. 19, 2017, which issued during the prosecution of Applicant's PCT/IL2016/051207.
An Office Action dated Feb. 28, 2014, which issued during the prosecution of U.S. Appl. No. 13/512,778.
An International Preliminary Report on Patentability dated Jan. 7, 2014, which issued during the prosecution of Applicant's PCT/IL2012/000269.
An International Preliminary Report on Patentability dated Jan. 4, 2012, which issued during the prosecution of Applicant's PCT/IB2010/052861.
An International Preliminary Report on Patentability dated Dec. 23, 2013, which issued during the prosecution of Applicant's PCT/IL2012/000241.
An International Preliminary Report on Patentability dated Aug. 6, 2013, which issued during the prosecution of Applicant's PCT/IL2012/000060.
An English translation of an Office Action dated Nov. 28, 2013, which issued during the prosecution of Chinese Patent Application No. 200880126889.0.
An English translation of an Office Action dated May 16, 2014, which issued during the prosecution of Chinese Patent Application No. 200880126889.0.
An English translation of an Office Action dated Feb. 16, 2013, which issued during the prosecution of Chinese Patent Application No. 200880126889.0.
An English translation of an Office Action dated Jan. 28, 2014, which issued during the prosecution of Chinese Patent Application No. 201080036970.7.
An International Preliminary Report on Patentability dated Jan. 10, 2012, which issued during the prosecution of Applicant's PCT/IL2010/000549.
An International Preliminary Report on Patentability dated Jan. 17, 2012, which issued during the prosecution of Applicant's PCT/IL2010/000564.
An Office Action dated Jul. 28, 2014, which issued during the prosecution of U.S. Appl. No. 13/031,871.
An International Preliminary Report on Patentability dated Jun. 12, 2012, which issued during the prosecution of Applicant's PCT/IL2010/001037.

(56) References Cited

OTHER PUBLICATIONS

An International Preliminary Report on Patentability dated Mar. 4, 2014, which issued during the prosecution of Applicant's PCT/IL2012/000300.
An International Preliminary Report on Patentability dated May 6, 2014, which issued during the prosecution of Applicant's PCT/IL2012/050424.
An International Preliminary Report on Patentability dated May 8, 2012, which issued during the prosecution of Applicant's PCT/IL2010/000917.
An International Preliminary Report on Patentability dated Nov. 18, 2014, which issued during the prosecution of Applicant's PCT/IL2012/000190.
A Notice of Allowance dated Aug. 2, 2012, which issued during the prosecution of U.S. Appl. No. 12/529,936.
An International Preliminary Report on Patentability dated Jun. 5, 2012, which issued during the prosecution of Applicant's PCT/IL2010/000999.
An International Preliminary Report on Patentability dated Jun. 5, 2012, which issued during the prosecution of Applicant's PCT/IL2010/001018.
An International Preliminary Report on Patentability dated Jun. 10, 2014, which issued during the prosecution of Applicant's PCT/IL2012/050506.
A Notice of Allowance issued in U.S. Appl. No. 13/807,906 dated Oct. 10, 2014.
A Restriction Requirement dated Jan. 29, 2014, which issued during the prosecution of U.S. Appl. No. 13/519,971.
An Advisory Action dated Feb. 13, 2014, which issued during the prosecution of U.S. Appl. No. 13/807,880.
An Office Action dated Jul. 24, 2014, which issued during the prosecution of Canadian Patent Application No. 2768228.
An International Search Report and a Written Opinion both dated Jul. 13, 2012, which issued during the prosecution of Applicant's PCT/IL2012/000083.
An International Search Report and a Written Opinion both dated Jul. 17, 2012, which issued during the prosecution of Applicant's PCT/IL2012/000095.
An Office Action dated Dec. 2, 2013, which issued during the prosecution of U.S. Appl. No. 13/807,880.
An International Search Report and a Written Opinion both dated Mar. 15, 2013, which issued during the prosecution of Applicant's PCT/IL2012/050424.
An Office Action dated May 20, 2013, which issued during the prosecution of U.S. Appl. No. 13/807,880.
Notice of Allowance dated Jun. 18, 2013, which issued during the prosecution of U.S. Appl. No. 13/523,296.
U.S. Appl. No. 61/505,132, filed Jul. 7, 2011.
An Office Action dated Apr. 10, 2014, which issued during the prosecution of Applicant's U.S. Patent Application No. 13/807,906.
An Office Action dated Apr. 24, 2014, which issued during the prosecution of Applicant's U.S. Patent Application No. 13/380,278.
An Office Action dated Apr. 28, 2014, which issued during the prosecution of Applicant's U.S. Patent Application No. 13/939,798.
Notice of Allowance dated Feb. 9, 2017, which issued during the prosecution of U.S. Appl. No. 14/772,016.
An Office Action dated Mar. 6, 2017, which issued during the prosecution of U.S. Appl. No. 13/979,551.
An Office Action dated Feb. 3, 2015, which issued during the prosecution of U.S. Appl. No. 12/447,684.
An International Preliminary Report on Patentability dated Feb. 3, 2015, which issued during the prosecution of Applicant's PCT/IL2013/050656.
A Notice of Allowance dated Jan. 7, 2014, which issued during the prosecution of U.S. Appl. No. 13/663,117.
European Search Report dated Oct. 31, 2014, which issued during the prosecution of Applicant'European App No. 12752054.2.
An Office Action dated Sep. 2, 2014, which issued during the prosecution of U.S. Appl. No. 12/447,684.
U.S. Appl. No. 61/448,199, filed Mar. 2, 2011.
An Office action dated Aug. 15, 2014, from the U.S. Patent and Trademark Office in counterpart U.S. Appl. No. 13/939,798.
U.S. Appl. No. 61/926,533, filed Jan. 13, 2014.
U.S. Appl. No. 61/528,242, filed Aug. 28, 2011.
U.S. Appl. No. 61/906,014, filed Nov. 19, 2013.
U.S. Appl. No. 61/775,964, filed Mar. 11, 2013.
U.S. Appl. No. 61/826,544, filed May 23, 2013.
U.S. Appl. No. 61/014,031, filed Dec. 15, 2007.
An Office Action dated Aug. 15, 2014, which issued during the prosecution of U.S. Appl. No. 13/512,778.
A Notice of Allowance dated Jan. 20, 2015, which issued during the prosecution of U.S. Appl. No. 13/383,128.
Notice of Allowance dated Nov. 7, 2014, which issued during the prosecution of U.S. Appl. No. 13/512,778.
International Preliminary Report on Patentability dated Aug. 21, 2013 in corresponding International Application No. PCT/IL2012/000083.
An Interview Summary dated Dec. 13, 2010, which issued during the prosecution of U.S. Appl. No. 12/447,684.
An Office Action dated Mar. 21, 2012, which issued during the prosecution of U.S. Appl. No. 12/808,037.
Notice of allowance dated May 22, 2013, which issued during the prosecution of U.S. Appl. No. 12/808,037.
U.S. Appl. No. 60/863,373, filed Oct. 29, 2006.
Notice of Allowance dated Dec. 19, 2014, which issued during the prosecution of U.S. Appl. No. 13/512,778.
An Office Action dated Sep. 11, 2015, which issued during the prosecution of U.S. Appl. No. 14/001,641.
An International Preliminary Report on Patentability dated Sep. 3, 2013, which issued during the prosecution of Applicant's PCT/IL2012/000095.
An International Search Report and a Written Opinion both dated Apr. 28, 2014, which issued during the prosecution of Applicant's PCT/IL2014/050019.
An Office action dated Sep. 4, 2014, from the U.S. Patent and Trademark Office in counterpart U.S. Appl. No. 13/519,971.
European Search Report dated Jun. 30, 2014, which issued during the prosecution of Applicant's European App No. 12741804.4.
Ryhanen J., in "Biocompatibility evaluation of nickel-titanium shape memory metal alloy," Academic Dissertation, Faculty of Medicine, Department of Surgery, University of Oulu, Finland (May 1999).
Notice of allowance dated Jun. 24, 2014, which issued during the prosecution of Applicant's U.S. Appl. No. 13/380,278.
An International Search Report dated Nov. 28, 2014, which issued during the prosecution of Applicant's PCT/IL2014/050434.
An Interview Summary dated Feb. 28, 2012, which issued during the prosecution of U.S. Appl. No. 12/529,936.
An Office Action dated Nov. 3, 2014, which issued during the prosecution of Canadian Patent Application No. 2767596.
An Office Action dated Nov. 19, 2013, which issued during the prosecution of U.S. Appl. No. 13/663,117.
Office Action dated Oct. 27, 2014 in Canadian Patent Application No. 2,785,953.
U.S. Appl. No. 61/678,182, filed Aug. 1, 2012.
U.S. Appl. No. 61/529,931, filed Sep. 1, 2011.
U.S. Appl. No. 61/553,209, filed Oct. 30, 2011.
U.S. Appl. No. 61/499,195, filed Jun. 21, 2011.
U.S. Appl. No. 61/749,965, filed Jan. 8, 2013.
U.S. Appl. No. 61/496,613, filed Jun. 14, 2011.
U.S. Appl. No. 61/221,074, filed Jun. 28, 2009.
U.S. Appl. No. 61/219,758, filed Jun. 23, 2009.
U.S. Appl. No. 61/264,861, filed Nov. 30, 2009.
An Interview Summary dated Sep. 25, 2014, which issued during the prosecution of U.S. Appl. No. 13/512,778.
An Interview Summary dated Apr. 24, 2014, which issued during the prosecution of U.S. Appl. No. 13/512,778.
An Office Action dated Jun. 18, 2013, which issued during the prosecution of U.S. Appl. No. 13/512,778.
Notice of Allowance dated Oct. 8, 2014, which issued during the prosecution of U.S. Appl. No. 13/512,778.
An Office Action dated Jan. 16, 2015, which issued during the prosecution of Chinese Patent Application No. 201080062714.5.

(56) References Cited

OTHER PUBLICATIONS

U.S. Appl. No. 62/093,497, filed Dec. 18, 2014.

* cited by examiner

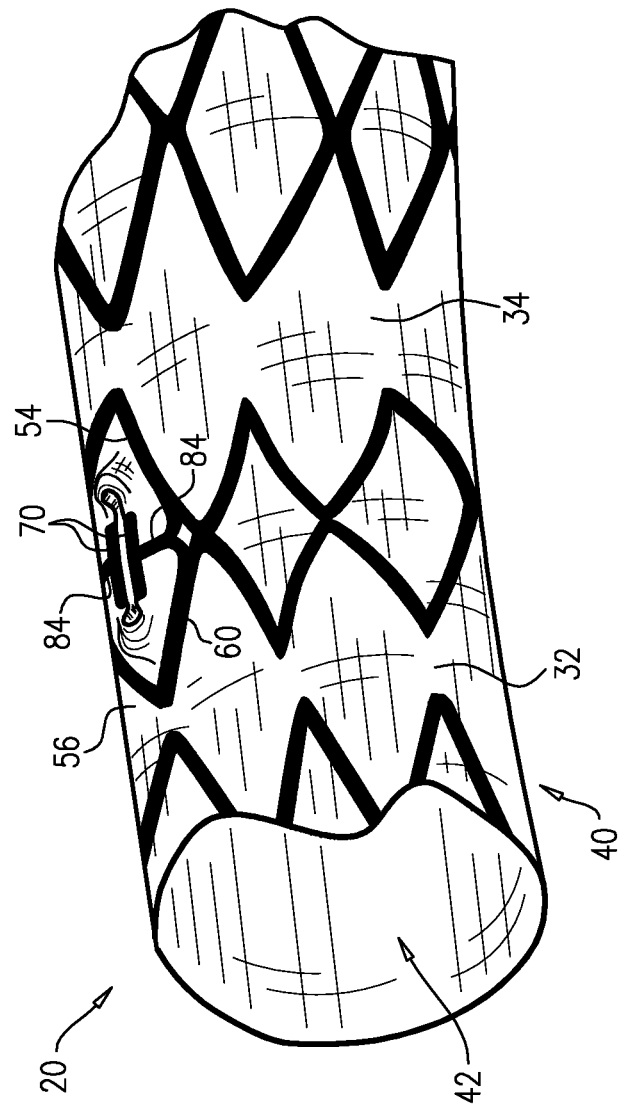

ENDOVASCULAR STENT-GRAFT WITH FATIGUE-RESISTANT LATERAL TUBE

CROSS-REFERENCE TO RELATED APPLICATIONS

The present application is the US national stage of International Application PCT/IL2015/051221, filed Dec. 16, 2015, which claims priority from U.S. Provisional Application 62/093,497, filed Dec. 18, 2014, which is assigned to the assignee of the present application and the above-mentioned applications are incorporated herein by reference.

FIELD OF THE APPLICATION

The present invention relates generally to implantable medical devices, and specifically to delivery tools and implantable stent-grafts.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms. A TAA may occur downstream the aortic arch, i.e., in the descending aorta. Alternatively, a TAA may occur in the aortic arch itself, where the aorta branches to supply the brachiocephalic, left carotid and subclavian arteries, or may occur in the ascending aorta.

Endo-Vascular Aneurysm Repair (EVAR) has transformed the practice of treatment of aortic aneurysms from an open surgical approach to a much less invasive surgical approach. The first step of an endovascular intervention usually requires introducing a delivery system into the vasculature of a subject. If the crossing profile, i.e., the external diameter, of the delivery system is 24 Fr or lower (3 Fr=1 millimeter), a true percutaneous approach may be used, because vascular closure devices are available for proper closure of such puncture sites.

Blood vessels occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally-invasive surgical procedures. An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

Aortic dissection is a tear or partial tear in the inner wall of the aorta, which causes blood to flow between the layers of the wall of the aorta, forcing the layers apart. Aortic dissections may be divided into two types in accordance with the Stanford classification: Type A dissections involve the ascending aorta and/or aortic arch, and possibly the descending aorta. Type B dissections involve the descending aorta or the arch (distal to right brachiocephalic artery origin), without involvement of the ascending aorta.

SUMMARY OF THE APPLICATION

In some embodiments of the present invention, a stent-graft comprises a plurality of structural strut members and a graft member, which are arranged so as to define a main tube and a lateral tube, when the stent-graft is in a radially-expanded state. The lateral tube has a proximal end that is joined to a lateral wall of the main tube. When the stent-graft is in the radially-expanded state, the structural strut members that the define lateral tube are shaped so as to define two to six, typically two to four, non-contiguous arcuate members, which (a) are centered around a central longitudinal axis of the lateral tube, and (b) collectively subtend at least 150 degrees around the central longitudinal axis. Typically, the arcuate members are arranged so as to provide respective circumferential gaps between circumferentially-adjacent ones of the arcuate members, when the stent-graft is in the radially-expanded state. This configuration of the structural stent members of the lateral tube tends to increase the fatigue resistance of the lateral tube during long-term implantation of the stent-graft in an aneurysmal artery.

For some applications, the structural strut members that define the lateral tube are shaped so as to define respective linking members for the arcuate members. The linking members link the arcuate members to the a junction at which the proximal end of the lateral tube is joined to the main tube, such as with one or more structural strut members that surround the proximal end of the lateral tube. For some of these applications, the linking members form respective angles with the respective arcuate members, which angles have an average of 30 to 90 degrees, when the stent-graft is in the radially-expanded state. In some configurations, the average angle is 85 to 90 degrees, e.g., 90 degrees, while for other applications, the average angle is 30 to 60 degrees, e.g., about 45 degrees.

For some applications, the arcuate members are disposed at a same axial position along the lateral tube, when the stent-graft is in the radially-expanded state. Typically, the arcuate members are disposed with 3 mm of a distal end of the structural strut members that define the lateral tube, when the stent-graft is in the radially-expanded state. For example, the arcuate members may be disposed at the distal end of the structural strut members that define the lateral tube, when the stent-graft is in the radially-expanded state. Typically, the arcuate members are disposed with 3 mm of a distal end of a portion of the graft member that defines the lateral tube, when the stent-graft is in the radially-expanded state. For example, the arcuate members may be disposed at the distal end of the portion of the graft member that defines the lateral tube, when the stent-graft is in the radially-expanded state.

There is therefore provided, in accordance with an inventive concept 1 of the present invention, apparatus comprising an endovascular stent-graft, which is configured to transition from a radially-compressed delivery state to a radially-expanded state, and which comprises:

a plurality of structural strut members; and a graft member, which comprises one or more substantially blood-impervious flexible sheets, and which is fixed to the structural strut members, wherein the structural strut members and the graft member are arranged so as to define, when the stent-graft is in the radially-expanded state:

a main tube, which is shaped so as to define a main lumen, and a lateral tube, which (a) has (i) a distal end and (ii) a proximal end that is joined to a lateral wall of the main tube at a junction, (b) is shaped so as to define a lateral lumen that is in fluid communication with the main lumen, and (c) defines a central longitudinal axis, and wherein, when the stent-graft is in the radially-expanded state, the structural strut members that define the lateral tube are shaped so as to define two to four non-contiguous arcuate members, which (a) are centered around the central longitudinal axis, and (b) collectively subtend at least 150 degrees around the central longitudinal axis.

Inventive concept 2. The apparatus according to inventive concept 1, wherein the arcuate members collectively subtend at least 180 degrees around the central longitudinal axis, when the stent-graft is in the radially-expanded state.

Inventive concept 3. The apparatus according to inventive concept 2, wherein the arcuate members collectively subtend at least 210 degrees around the central longitudinal axis, when the stent-graft is in the radially-expanded state.

Inventive concept 4. The apparatus according to inventive concept 1, wherein at least one of the arcuate members alone subtends at least 60 degrees around the central longitudinal axis, when the stent-graft is in the radially-expanded state.

Inventive concept 5. The apparatus according to inventive concept 1, wherein the arcuate members are disposed at a same axial position along the lateral tube, when the stent-graft is in the radially-expanded state.

Inventive concept 6. The apparatus according to inventive concept 1, wherein at least two of the arcuate members are disposed at respective different axial positions along the lateral tube, when the stent-graft is in the radially-expanded state.

Inventive concept 7. The apparatus according to inventive concept 1, wherein the arcuate members are disposed with 3 mm of a distal end of the structural strut members that define the lateral tube, when the stent-graft is in the radially-expanded state.

Inventive concept 8. The apparatus according to inventive concept 7, wherein the arcuate members are disposed at the distal end of the structural strut members that define the lateral tube, when the stent-graft is in the radially-expanded state.

Inventive concept 9. The apparatus according to inventive concept 1, wherein the arcuate members are disposed with 3 mm of a distal end of a portion of the graft member that defines the lateral tube, when the stent-graft is in the radially-expanded state.

Inventive concept 10. The apparatus according to inventive concept 9, wherein the arcuate members are disposed at the distal end of the portion of the graft member that defines the lateral tube, when the stent-graft is in the radially-expanded state.

Inventive concept 11. The apparatus according to inventive concept 1, wherein when the main tube is in a radially-expanded state thereof and the lateral tube is in a compressed delivery state thereof, the arcuate members define a portion of a generally tubular outer surface of the main tube.

Inventive concept 12. The apparatus according to inventive concept 1, wherein the apparatus further comprises a branching stent-graft, which is configured to form a blood-tight seal with the lateral tube, when the stent-graft is in the radially-expanded state and the branching stent-graft is in a radially-expanded state.

Inventive concept 13. The apparatus according to inventive concept 1, wherein a ratio of (a) an average circumference of the main tube and (b) an average circumference of the lateral tube is between 1:1 and 5:1, when the stent-graft is in the radially-expanded state.

Inventive concept 14. The apparatus according to inventive concept 1, wherein a length of the lateral tube is between 10% and 30% of an average circumference of the lateral tube, when the stent-graft is in the radially-expanded state.

Inventive concept 15. The apparatus according to inventive concept 1, wherein a circumference of the lateral tube at the proximal end of the lateral tube is between 5% and 30% greater than a circumference of the lateral tube at the distal end of the lateral tube, when the stent-graft is in the radially-expanded state.

Inventive concept 16. The apparatus according to inventive concept 1, wherein an angle between the central longitudinal axis of the lateral tube and a central longitudinal axis of the main tube is greater than 80 degrees, when the stent-graft is in the radially-expanded state.

Inventive concept 17. The apparatus according to inventive concept 1, wherein an angle between the central longitudinal axis of the lateral tube and a central longitudinal axis of the main tube is between 60 and 80 degrees, when the stent-graft is in the radially-expanded state.

Inventive concept 18. The apparatus according to inventive concept 1, wherein an angle between the central longitudinal axis of the lateral tube and a central longitudinal axis of the main tube is between 30 and 60 degrees, when the stent-graft is in the radially-expanded state.

Inventive concept 19. The apparatus according to inventive concept 1, wherein the main tube has proximal and distal ends, and wherein a circumference of the proximal end of the main tube is 3 to 10 cm, when the stent-graft is in the radially-expanded state.

Inventive concept 20. The apparatus according to inventive concept 19, wherein a circumference of the distal end of the main tube is 6 to 12 cm, when the stent-graft is in the radially-expanded state.

Inventive concept 21. The apparatus according to inventive concept 1, wherein a length of the main tube is 4 to 15 cm.

Inventive concept 22. The apparatus according to inventive concept 1, wherein the one or more of the structural strut members comprise a flexible metal.

Inventive concept 23. The apparatus according to inventive concept 22, wherein the metal comprises a superelastic alloy.

Inventive concept 24. The apparatus according to inventive concept 23, wherein the alloy comprises Nitinol.

Inventive concept 25. The apparatus according to inventive concept 1, wherein the one or more flexible sheets comprise polyethylene terephthalate.

Inventive concept 26. The apparatus according to inventive concept 1, wherein the one or more flexible sheets comprise expanded polytetrafluoroethylene (PTFE).

Inventive concept 27. The apparatus according to any one of inventive concepts 1-26, wherein the arcuate members are arranged so as to provide respective circumferential gaps between circumferentially-adjacent ones of the arcuate members, when the stent-graft is in the radially-expanded state.

Inventive concept 28. The apparatus according to inventive concept 27, wherein the arcuate members collectively subtend no more than 350 degrees around the central longitudinal axis, when the stent-graft is in the radially-expanded state.

Inventive concept 29. The apparatus according to inventive concept 28, wherein the arcuate members collectively subtend no more than 340 degrees around the central longitudinal axis, when the stent-graft is in the radially-expanded state.

Inventive concept 30. The apparatus according to inventive concept 27, wherein each of the circumferential gaps measures at least 10 degrees, when the stent-graft is in the radially-expanded state.

Inventive concept 31. The apparatus according to inventive concept 30, wherein each of the circumferential gaps measures at least 20 degrees, when the stent-graft is in the radially-expanded state.

Inventive concept 32. The apparatus according to inventive concept 27, wherein the arcuate members are disposed at a same axial position along the lateral tube, when the stent-graft is in the radially-expanded state.

Inventive concept 33. The apparatus according to inventive concept 32, wherein respective areas of the lateral tube, which (a) circumferentially correspond with the gaps and (b) extend from the axial position of the arcuate members along at least 50% of a distance between the axial position of the arcuate members and the junction, are free from the structural strut members, when the stent-graft is in the radially-expanded state.

Inventive concept 34. The apparatus according to inventive concept 33, wherein the respective areas extend from the arcuate members along 60% of the distance.

Inventive concept 35. The apparatus according to inventive concept 34, wherein the respective areas extend from the arcuate members along 100% of the distance.

Inventive concept 36. The apparatus according to any one of inventive concepts 1-26, wherein the structural strut members that define the lateral tube are shaped so as to define respective linking members for the arcuate members, which linking members link the arcuate members to the junction.

Inventive concept 37. The apparatus according to inventive concept 36, wherein, when the stent-graft is in the radially-expanded state, the lateral tube is free from the structural strut members, except for the arcuate members and the linking members, in an area that (a) extends entirely around the central longitudinal axis and (b) extends from the distal end of the lateral tube along at least 50% of a distance between the distal end of the lateral tube and the junction.

Inventive concept 38. The apparatus according to inventive concept 37, wherein, when the stent-graft is in the radially-expanded state, the lateral tube is free from the structural strut members, except for the arcuate members, the linking members, and any of the structural strut members that surround the proximal end of the lateral tube at the junction.

Inventive concept 39. The apparatus according to inventive concept 36, wherein an average length of the linking members equals at least 80% of a length of the lateral tube, when the stent-graft is in the radially-expanded state.

Inventive concept 40. The apparatus according to inventive concept 36, wherein, when the stent-graft is in the radially-expanded state, respective points on the linking members and respective juncture points between the link members and the arcuate members define respective lines, which lines form respective angles with the respective arcuate members, which angles have an average of 30 to 90 degrees, and which points on the linking members are at 30% of a distance between the axial position of the arcuate members and the junction.

Inventive concept 41. The apparatus according to inventive concept 40, wherein an average length of the linking members equals at least 80% of a length of the lateral tube, when the stent-graft is in the radially-expanded state.

Inventive concept 42. The apparatus according to inventive concept 40, wherein the average is 85 to 90 degrees.

Inventive concept 43. The apparatus according to inventive concept 42, wherein the average is 90 degrees.

Inventive concept 44. The apparatus according to inventive concept 40, wherein the average is 30 to 60 degrees.

Inventive concept 45. The apparatus according to inventive concept 40, wherein the linking members form respective angles with the respective arcuate members, which angles have an average of 30 to 90 degrees, when the stent-graft is in the radially-expanded state.

Inventive concept 46. The apparatus according to inventive concept 45, wherein the average is 85 to 90 degrees.

Inventive concept 47. The apparatus according to inventive concept 46, wherein the average is 90 degrees.

Inventive concept 48. The apparatus according to inventive concept 45, wherein the average is 30 to 60 degrees.

Inventive concept 49. The apparatus according to inventive concept 36, wherein each of the linking members is connected to its respective arcuate member at a juncture point at a location along the arcuate member that is within a number of degrees of a circumferential center of the arcuate member around the central circumferential axis, which number of degrees is equal to 40% of a total number of degrees of the arcuate member.

Inventive concept 50. The apparatus according to inventive concept 49, wherein the location along the arcuate member is at the circumferential center of the arcuate member.

Inventive concept 51. The apparatus according to inventive concept 36, wherein, when the stent-graft is in the radially-expanded state, one or more of the structural strut members (a) completely surround the proximal end of the lateral tube at the junction and (b) are connected to the linking members.

Inventive concept 52. The apparatus according to any one of inventive concepts 1-26, wherein one or more of the structural strut members completely surround the proximal end of the lateral tube at the junction, when the stent-graft is in the radially-expanded state.

Inventive concept 53. The apparatus according to inventive concept 52,
wherein the structural strut members that define the main tube are shaped so as a plurality of circumferential stent springs, each of which is shaped so as to define a plurality of stent cells, and
wherein one of the stent cells of one of the circumferential stent springs is defined by the one or more of the structural strut members that completely surround the proximal end of the lateral tube at the junction, when the stent-graft is in the radially-expanded state.

Inventive concept 54. The apparatus according to inventive concept 53, wherein the stent cells of the one of the circumferential stent springs are diamond-shaped, when the stent-graft is in the radially-expanded state.

Inventive concept 55. The apparatus according to inventive concept 54, wherein the diamond-shaped stent cells have respective, different dimensions, when the stent-graft is in the radially-expanded state.

Inventive concept 56. The apparatus according to inventive concept 55, wherein a largest one of the diamond-shaped stent cells is at least 100% greater in surface area than a smallest one of the diamond-shaped stent cells, which largest one of the diamond-shaped stent cells is the one of the stent cells that is defined by the one or more of the structural strut members that completely surround the proximal end of the lateral tube at the junction, when the stent-graft is in the radially-expanded state.

Inventive concept 57. The apparatus according to inventive concept 56,

Inventive concept wherein the lateral tube is a first lateral tube, the distal and proximal ends are first distal and proximal ends, the junction is a first junction, the lateral lumen is a first lateral lumen, the central longitudinal axis is a first central longitudinal axis, and the arcuate members are first arcuate members, wherein the structural strut members and the graft member are arranged so as to define, when the stent-graft is in the radially-expanded state, a second lateral tube, which (a) has (i) a second distal end and (ii) a second proximal end that is joined to the lateral wall of the main tube at a second junction, (b) is shaped so as to define a second lateral lumen that is in fluid communication with the main lumen, and (c) defines a second central longitudinal axis, wherein, when the stent-graft is in the radially-expanded state, the structural strut members that define the second lateral tube are shaped so as to define two to four non-contiguous second arcuate members, which (a) are centered around the second central longitudinal axis, and (b) collectively subtend at least 150 degrees around the second central longitudinal axis, and wherein the smallest one of the diamond-shaped stent cells completely surrounds the second proximal end of the second lateral tube at the second junction, when the stent-graft is in the radially-expanded state.

There is further provided, in accordance with an inventive concept 58 of the present invention, a method for treating a subject, comprising:

transvascularly introducing an endovascular stent-graft into a blood vessel of the subject while the stent-graft is in a radially-compressed delivery state, which stent-graft comprises (a) a plurality of structural strut members, and (b) a graft member, which comprises one or more substantially blood-impervious flexible sheets, and which is fixed to the structural strut members; and transitioning the stent-graft to a radially-expanded state, in which:

the structural strut members and the graft member are arranged so as to define (x) a main tube, which is shaped so as to define a main lumen, and (y) a lateral tube, which (a) has (i) a distal end and (ii) a proximal end that is joined to a lateral wall of the main tube at a junction, (b) is shaped so as to define a lateral lumen that is in fluid communication with the main lumen, and (c) defines a central longitudinal axis, and the structural strut members that define the lateral tube are shaped so as to define two to four non-contiguous arcuate members, which (a) are centered around the central longitudinal axis, and (b) collectively subtend at least 150 degrees around the central longitudinal axis.

Inventive concept 59. The method according to inventive concept 58, wherein transitioning comprises transitioning the stent-graft to the radially-expanded state in which the arcuate members collectively subtend at least 180 degrees around the central longitudinal axis.

Inventive concept 60. The method according to inventive concept 59, wherein transitioning comprises transitioning the stent-graft to the radially-expanded state in which the arcuate members collectively subtend at least 210 degrees around the central longitudinal axis.

Inventive concept 61. The method according to inventive concept 58, wherein transitioning comprises transitioning the stent-graft to the radially-expanded state in which at least one of the arcuate members alone subtends at least 60 degrees around the central longitudinal axis.

Inventive concept 62. The method according to inventive concept 58, wherein transitioning comprises transitioning the stent-graft to the radially-expanded state in which the arcuate members are disposed at a same axial position along the lateral tube.

Inventive concept 63. The method according to inventive concept 58, wherein transitioning comprises transitioning the stent-graft to the radially-expanded state in which at least two of the arcuate members are disposed at respective different axial positions along the lateral tube.

Inventive concept 64. The method according to inventive concept 58, wherein transitioning comprises transitioning the stent-graft to the radially-expanded state in which the arcuate members are disposed with 3 mm of a distal end of the structural strut members that define the lateral tube.

Inventive concept 65. The method according to inventive concept 64, wherein transitioning comprises transitioning the stent-graft to the radially-expanded state in which the arcuate members are disposed at the distal end of the structural strut members that define the lateral tube.

Inventive concept 66. The method according to inventive concept 58, wherein transitioning comprises transitioning the stent-graft to the radially-expanded state in which the arcuate members are disposed with 3 mm of a distal end of a portion of the graft member that defines the lateral tube.

Inventive concept 67. The method according to inventive concept 66, wherein transitioning comprises transitioning the stent-graft to the radially-expanded state in which the arcuate members are disposed at the distal end of the portion of the graft member that defines the lateral tube.

Inventive concept 68. The method according to inventive concept 58, wherein transitioning comprises:

transitioning the main tube to a radially-expanded state thereof while the lateral tube remains in a compressed delivery state thereof, in which the arcuate members define a portion of a generally tubular outer surface of the main tube; and thereafter, transitioning the lateral tube to a radially-expanded state thereof, such that the stent-graft is in the radially-expanded state thereof.

Inventive concept 69. The method according to inventive concept 58, wherein transitioning comprises transitioning the stent-graft to the radially-expanded state in which a ratio of (a) an average circumference of the main tube and (b) an average circumference of the lateral tube is between 1:1 and 5:1.

Inventive concept 70. The method according to inventive concept 58, wherein transitioning comprises transitioning the stent-graft to the radially-expanded state in which a length of the lateral tube is between 10% and 30% of an average circumference of the lateral tube.

Inventive concept 71. The method according to inventive concept 58, wherein transitioning comprises transitioning the stent-graft to the radially-expanded state in which a circumference of the lateral tube at the proximal end of the lateral tube is between 5% and 30% greater than a circumference of the lateral tube at the distal end of the lateral tube.

Inventive concept 72. The method according to inventive concept 58, wherein transitioning comprises transitioning the stent-graft to the radially-expanded state in which an angle between the central longitudinal axis of the lateral tube and a central longitudinal axis of the main tube is greater than 80 degrees.

Inventive concept 73. The method according to inventive concept 58, wherein transitioning comprises transitioning the stent-graft to the radially-expanded state in which an angle between the central longitudinal axis of the lateral tube and a central longitudinal axis of the main tube is between 60 and 80 degrees.

Inventive concept 74. The method according to inventive concept 58, wherein transitioning comprises transitioning the stent-graft to the radially-expanded state in which an angle between the central longitudinal axis of the lateral tube and a central longitudinal axis of the main tube is between 30 and 60 degrees.

Inventive concept 75. The method according to inventive concept 58, wherein the main tube has proximal and distal ends, and wherein transitioning comprises transitioning the stent-graft to the radially-expanded state in which a circumference of the proximal end of the main tube is 3 to 10 cm.

Inventive concept 76. The method according to inventive concept 75, wherein transitioning comprises transitioning the stent-graft to the radially-expanded state in which a circumference of the distal end of the main tube is 6 to 12 cm.

Inventive concept 77. The method according to inventive concept 58, wherein transvascularly introducing the stent-graft comprises transvascularly introducing the stent-graft while the stent-graft is restrained in the radially-compressed delivery state within an elongate delivery tube, and wherein transitioning the stent-graft to a radially-expanded state comprises releasing the stent-graft from the elongate delivery tube.

Inventive concept 78. The method according to inventive concept 77, wherein a ratio of (a) an average circumference of the main tube when in a radially-expanded state thereof to (b) an inner circumference of the delivery tube is at least 5.

Inventive concept 79. The method according to inventive concept 58, wherein transitioning comprises transitioning the stent-graft to the radially-expanded state in which the arcuate members are arranged so as to provide respective circumferential gaps between circumferentially-adjacent ones of the arcuate members.

Inventive concept 80. The method according to inventive concept 79, wherein transitioning comprises transitioning the stent-graft to the radially-expanded state in which the arcuate members collectively subtend no more than 350 degrees around the central longitudinal axis.

Inventive concept 81. The method according to inventive concept 80, wherein transitioning comprises transitioning the stent-graft to the radially-expanded state in which the arcuate members collectively subtend no more than 340 degrees around the central longitudinal axis.

Inventive concept 82. The method according to inventive concept 79, wherein transitioning comprises transitioning the stent-graft to the radially-expanded state in which each of the circumferential gaps measures at least 10 degrees.

Inventive concept 83. The method according to inventive concept 82, wherein transitioning comprises transitioning the stent-graft to the radially-expanded state in which each of the circumferential gaps measures at least 20 degrees.

Inventive concept 84. The method according to inventive concept 79, wherein transitioning comprises transitioning the stent-graft to the radially-expanded state in which the arcuate members are disposed at a same axial position along the lateral tube.

Inventive concept 85. The method according to inventive concept 84, wherein transitioning comprises transitioning the stent-graft to the radially-expanded state in which respective areas of the lateral tube, which (a) circumferentially correspond with the gaps and (b) extend from the axial position of the arcuate members along at least 50% of a distance between the axial position of the arcuate members and the junction, are free from the structural strut members.

Inventive concept 86. The method according to inventive concept 85, wherein transitioning comprises transitioning the stent-graft to the radially-expanded state in which the respective areas extend from the arcuate members along 60% of the distance.

Inventive concept 87. The method according to inventive concept 86, wherein transitioning comprises transitioning the stent-graft to the radially-expanded state in which the respective areas extend from the arcuate members along 100% of the distance.

Inventive concept 88. The method according to inventive concept 58, wherein the structural strut members that define the lateral tube are shaped so as to define respective linking members for the arcuate members, which linking members link the arcuate members to the junction.

Inventive concept 89. The method according to inventive concept 88, wherein transitioning comprises transitioning the stent-graft to the radially-expanded state in which the lateral tube is free from the structural strut members, except for the arcuate members and the linking members, in an area that (a) extends entirely around the central longitudinal axis and (b) extends from the distal end of the lateral tube along at least 50% of a distance between the distal end of the lateral tube and the junction.

Inventive concept 90. The method according to inventive concept 89, wherein transitioning comprises transitioning the stent-graft to the radially-expanded state in which the lateral tube is free from the structural strut members, except for the arcuate members, the linking members, and any of the structural strut members that surround the proximal end of the lateral tube at the junction.

Inventive concept 91. The method according to inventive concept 88, wherein transitioning comprises transitioning the stent-graft to the radially-expanded state in which an average length of the linking members equals at least 80% of a length of the lateral tube.

Inventive concept 92. The method according to inventive concept 88, wherein transitioning comprises transitioning the stent-graft to the radially-expanded state in which respective points on the linking members and respective juncture points between the link members and the arcuate members define respective lines, which lines form respective angles with the respective arcuate members, which angles have an average of 30 to 90 degrees, and which points on the linking members are at 30% of a distance between the axial position of the arcuate members and the junction.

Inventive concept 93. The method according to inventive concept 92, wherein transitioning comprises transitioning the stent-graft to the radially-expanded state in which an average length of the linking members equals at least 80% of a length of the lateral tube.

Inventive concept 94. The method according to inventive concept 92, wherein the average is 85 to 90 degrees.

Inventive concept 95. The method according to inventive concept 94, wherein the average is 90 degrees.

Inventive concept 96. The method according to inventive concept 92, wherein the average is 30 to 60 degrees.

Inventive concept 97. The method according to inventive concept 92, wherein transitioning comprises transitioning the stent-graft to the radially-expanded state in which the linking members form respective angles with the respective arcuate members, which angles have an average of 30 to 90 degrees.

Inventive concept 98. The method according to inventive concept 97, wherein the average is 85 to 90 degrees.

Inventive concept 99. The method according to inventive concept 98, wherein the average is 90 degrees.

Inventive concept 100. The method according to inventive concept 97, wherein the average is 30 to 60 degrees.

Inventive concept 101. The method according to inventive concept 88, wherein transitioning comprises transitioning the stent-graft to the radially-expanded state in which each of the linking members is connected to its respective arcuate member at a juncture point at a location along the arcuate member that is within a number of degrees of a circumferential center of the arcuate member around the central circumferential axis, which number of degrees is equal to 40% of a total number of degrees of the arcuate member.

Inventive concept 102. The method according to inventive concept 101, wherein the location along the arcuate member is at the circumferential center of the arcuate member.

Inventive concept 103. The method according to inventive concept 88, wherein transitioning comprises transitioning the stent-graft to the radially-expanded state in which one or more of the structural strut members (a) completely surround the proximal end of the lateral tube at the junction and (b) are connected to the linking members.

Inventive concept 104. The method according to inventive concept 58, wherein transitioning comprises transitioning the stent-graft to the radially-expanded state in which one or more of the structural strut members completely surround the proximal end of the lateral tube at the junction.

Inventive concept 105. The method according to inventive concept 104, wherein the structural strut members that define the main tube are shaped so as a plurality of circumferential stent springs, each of which is shaped so as to define a plurality of stent cells, and wherein transitioning comprises transitioning the stent-graft to the radially-expanded state in which one of the stent cells of one of the circumferential stent springs is defined by the one or more of the structural strut members that completely surround the proximal end of the lateral tube at the junction.

Inventive concept 106. The method according to inventive concept 105, wherein transitioning comprises transitioning the stent-graft to the radially-expanded state in which the stent cells of the one of the circumferential stent springs are diamond-shaped.

Inventive concept 107. The method according to inventive concept 106, wherein transitioning comprises transitioning the stent-graft to the radially-expanded state in which the diamond-shaped stent cells have respective, different dimensions.

Inventive concept 108. The method according to inventive concept 107, wherein transitioning comprises transitioning the stent-graft to the radially-expanded state in which a largest one of the diamond-shaped stent cells is at least 100% greater in surface area than a smallest one of the diamond-shaped stent cells, which largest one of the diamond-shaped stent cells is the one of the stent cells that is defined by the one or more of the structural strut members that completely surround the proximal end of the lateral tube at the junction.

109. The method according to inventive concept 108, wherein the lateral tube is a first lateral tube, the distal and proximal ends are first distal and proximal ends, the junction is a first junction, the lateral lumen is a first lateral lumen, the central longitudinal axis is a first central longitudinal axis, and the arcuate members are first arcuate members, wherein transitioning comprises transitioning the stent-graft to the radially-expanded state, in which:

the structural strut members and the graft member are arranged so as to define a second lateral tube, which (a) has (i) a second distal end and (ii) a second proximal end that is joined to the lateral wall of the main tube at a second junction, (b) is shaped so as to define a second lateral lumen that is in fluid communication with the main lumen, and (c) defines a second central longitudinal axis, and the structural strut members that define the second lateral tube are shaped so as to define two to four non-contiguous second arcuate members, which (a) are centered around the second central longitudinal axis, and (b) collectively subtend at least 150 degrees around the second central longitudinal axis, and wherein the smallest one of the diamond-shaped stent cells completely surrounds the second proximal end of the second lateral tube at the second junction, when the stent-graft is in the radially-expanded state.

Inventive concept 110. The method according to inventive concept 58, wherein transvascularly introducing the stent-graft into the blood vessel comprises transvascularly introducing the stent-graft into an aorta of the subject.

Inventive concept 111. The method according to inventive concept 110, wherein transvascularly introducing the stent-graft into the aorta comprises transvascularly introducing the stent-graft into an aneurysmal aorta.

Inventive concept 112. The method according to inventive concept 58, further comprising:

transvascularly introducing a branching stent-graft through a portion of the main tube and into a branching blood vessel while the branching stent-graft is in a radially-compressed delivery state thereof; and transitioning the branching stent-graft to a radially-expanded state thereof, in which the branching stent-graft forms a blood-tight seal with the lateral tube.

Inventive concept 113. The method according to inventive concept 112, wherein transvascularly introducing the stent-graft into the blood vessel comprises transvascularly introducing the stent-graft into an aneurysmal aorta of the subject, and wherein transvascularly introducing the branching stent-graft into the branching blood vessel comprises transvascularly introducing the branching stent-graft into a visceral artery of the subject.

Inventive concept 114. The method according to inventive concept 113, wherein the visceral artery is a renal artery.

Inventive concept 115. The method according to inventive concept 113, wherein the visceral artery is a superior mesenteric artery (SMA).

Inventive concept 116. The method according to inventive concept 113, wherein the visceral artery is a celiac artery.

The present invention will be more fully understood from the following detailed description of embodiments thereof, taken together with the drawings, in which:

BRIEF DESCRIPTION OF THE DRAWINGS

FIGS. 1A-B are schematic illustrations of a portion of an endovascular stent-graft, in accordance with an application of the present invention;

DETAILED DESCRIPTION OF APPLICATIONS

Figure 1A:
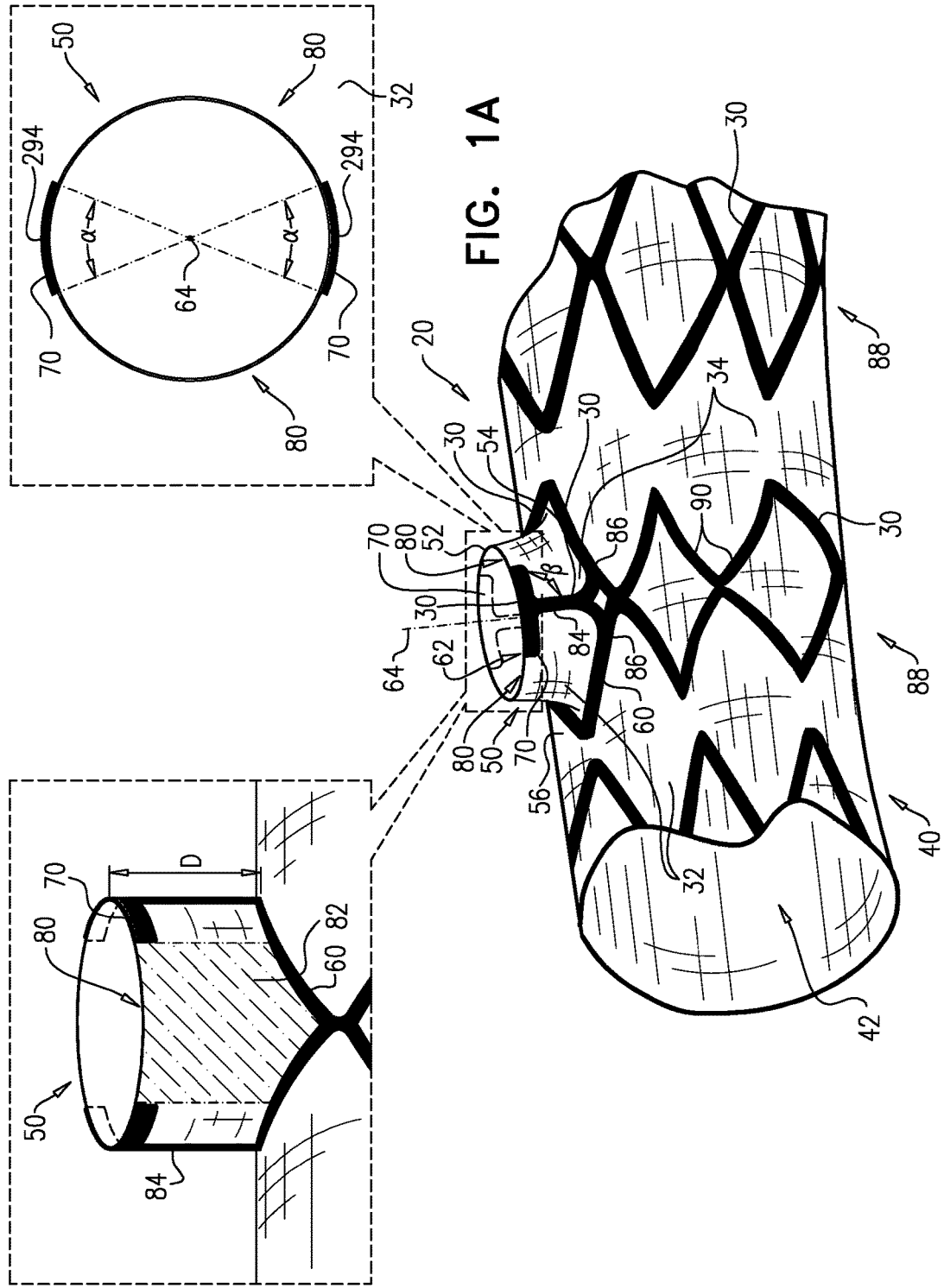

FIGS. 1A and 1B are schematic illustrations of a portion of an endovascular stent-graft 20, in accordance with an application of the present invention. Stent-graft 20 is configured to transition from a radially-compressed delivery state (not shown) to a radially-expanded state (as shown in FIG. 1A). Stent-graft 20 comprises a plurality of structural strut members 30 and a graft member 32, which is fixed to structural strut members 30.

Structural strut members 30 and graft member 32 are arranged so as to define, when stent-graft 20 is in the radially-expanded state:
 a main tube 40, which is shaped so as to define a main lumen 42, and
 a lateral tube 50, which (a) has (i) a distal end 52 and (ii) a proximal end 54 that is joined to a lateral wall 56 of main tube 40 at a junction 60 (junction 60 is flush with the external surface of main tube 40), (b) is shaped so as to define a lateral lumen 62 that is in fluid communication with main lumen 42, and (c) defines a central longitudinal axis 64.

When stent-graft 20 is in the radially-expanded state, as shown in FIG. 1A, structural strut members 30 that define lateral tube 50 are shaped so as to define two to six, typically two to four, non-contiguous arcuate members 70, which (a) are centered around central longitudinal axis 64, and (b) collectively subtend at least 150 degrees around central longitudinal axis 64, such as at least 180 degrees, e.g., at least 210 degrees around central longitudinal axis 64, such as at least 300 degrees, e.g., at least 340 degrees. (It is to be understood that not all of structural strut members 30 that define lateral tube 50 necessarily are shaped so as to define arcuate members 70; typically, only a portion of structural strut members 30 that define lateral tube 50 are shaped so as to define arcuate members 70.) For example, in the configuration shown in FIGS. 1A and 1B, structural strut members 30 that define lateral tube 50 are shaped so as to define exactly two non-contiguous arcuate members 70, each of which subtends an angle α (alpha) around central longitudinal axis 64, such that they collectively subtend an angle equal to 2α (twice alpha). For some applications, at least one of arcuate members 70 alone subtends at least 60 degrees around central longitudinal axis 64 when stent-graft 20 is in the radially-expanded state. For example, in the configuration shown in FIGS. 1A and 1B, angle α (alpha) is greater than 60 degrees, such that each of the arcuate members, taken separately, subtends at least 60 degrees around central longitudinal axis 64.

For some applications, stent-graft 20 is self-expanding, in which case the radially-expanded state is a relaxed state of the stent-graft. For these applications, lateral tube 50 is typically self-protruding from main tube 40. As used in the present application, including in the claims, a "central longitudinal axis" of an elongate structure is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.)

Typically, structural strut members 30 comprise a metal, such as a flexible metal, an elastic metal, stainless steel, or a superelastic alloy (such as Nitinol). Graft member 32 comprises one or more biologically-compatible substantially blood-impervious flexible sheets 34, and is attached (such as by stitching) to at least a portion of structural strut members 30, on either side of the surfaces defined by the support element, so as to define lumens 42 and 62. The flexible sheets may comprise, for example, a polymeric material (e.g., a polyester, or polytetrafluoroethylene), a textile material (e.g., polyethylene terephthalate (PET), or expanded polytetrafluoroethylene (ePTFE)), natural tissue (e.g., saphenous vein or collagen), or a combination thereof.

Typically, arcuate members 70 are disposed with 3 mm of a distal end of structural strut members 30 that define lateral tube 50, when stent-graft 20 is in the radially-expanded state. For example, arcuate members 70 may be disposed at the distal end of structural strut members 30 that define lateral tube 50, when stent-graft 20 is in the radially-expanded state, such as shown in FIG. 1A. Typically, arcuate members 70 are disposed with 3 mm of a distal end of a portion of graft member 32 that defines lateral tube 50, when stent-graft 20 is in the radially-expanded state. For example, arcuate members 70 may be disposed at the distal end of the portion of graft member 32 that defines lateral tube 50, when stent-graft 20 is in the radially-expanded state, such as shown in FIG. 1A.

FIG. 1B shows stent-graft 20 when main tube 40 is in a radially-expanded state thereof and lateral tube 50 is in a compressed delivery state thereof. For some applications, such as shown in FIG. 1B, when main tube 40 is in a radially-expanded state thereof and lateral tube 50 is in a compressed delivery state thereof, arcuate members 70 define a portion of a generally tubular outer surface of main tube 40.

Typically, arcuate members 70 are arranged so as to provide respective circumferential gaps 80 between circumferentially-adjacent ones of arcuate members 70, when stent-graft 20 is in the radially-expanded state. For example, in the configuration shown in FIG. 1A, arcuate members 70 are arranged so as to provide exactly two circumferential gaps 80. For some applications, arcuate members 70 collectively subtend no more than 350 degrees around central longitudinal axis 64, such as no more than 340 degrees, when stent-graft 20 is in the radially-expanded state. For example, as shown in FIG. 1A, in the configuration shown in FIGS. 1A and 1B, structural strut members 30 that define lateral tube 50 are shaped so as to define exactly two non-contiguous arcuate members 70, each of which subtends an angle α (alpha) around central longitudinal axis 64, such that they collectively subtend an angle equal to 2α (twice alpha), which is no more than 350 degrees. For some applications, each of the circumferential gaps measures at least 10 degrees, such as at least 20 degrees, when stent-graft 20 is in the radially-expanded state.

For some applications, such as shown in FIG. 1A (and in FIGS. 2A, 3A, 4A, and 5A-B, described hereinbelow), arcuate members 70 are disposed at a same axial position along lateral tube 50, when stent-graft 20 is in the radially-expanded state. For some of these applications, such as shown in FIG. 1A, respective areas 82 of lateral tube 50, which (a) circumferentially correspond with the gaps and (b) extend from the axial position of arcuate members 70 along at least 50%, such as at least 60%, e.g., 100% (as shown in FIG. 1A), of a distance D between the axial position of arcuate members 70 and junction 60, are free from structural strut members 30, when stent-graft 20 is in the radially-expanded state.

For some applications, one or more of structural strut members 30 (these one or more structural strut members are labeled 86 in the figures) surround proximal end 54 of lateral tube 50 at junction 60. For some applications, one or more of structural strut members 30 (these one or more structural strut members are labeled 86 in the figures) surround proximal end 54, such as completely (i.e., around 360 degrees) surround proximal end 54, when stent-graft 20 is in the radially-expanded state.

For some applications, structural strut members 30 that define lateral tube 50 are shaped so as to define respective linking members 84 for arcuate members 70. Linking members 84 link arcuate members 70 to junction 60, such as with the one or more structural strut members 86 that surround proximal end 54, for applications in which these surrounding strut members are provided. (It is to be understood that not all of structural strut members 30 that define lateral tube 50 necessarily are shaped so as to define linking members 84; typically, only a portion of structural strut members 30 that define lateral tube 50 are shaped so as to define linking members 84.) For some applications, linking members 84 form respective angles β (beta) with the respective arcuate members 70, which angles have an average of 30 to 90 degrees, such as 85 to 90 degrees. e.g., 90 degrees, when stent-graft 20 is in the radially-expanded state. For some applications, an average length of linking members 84 equals at least 80% of a length of lateral tube 50.

For some applications, such as shown in FIG. 1A (and in FIGS. 2A-B, 3A, 4A, and 5A-B, described hereinbelow), when stent-graft 20 is in the radially-expanded state, lateral tube 50 is free from structural strut members 30, except for arcuate members 70 and linking members 84, in an area that (a) extends entirely around central longitudinal axis 64 and (b) extends from distal end 52 of lateral tube 50 along at least 50% of a distance between distal end 52 of lateral tube 50 and junction 60. For some of these applications, such as also shown in FIG. 1A (and in FIGS. 2A-B, 3A, 4A, and 5A-B, described hereinbelow), when stent-graft 20 is in the radially-expanded state, lateral tube 50 is free from structural strut members 30, except for arcuate members 70, linking members 84, and any of structural strut members 30 that surround proximal end 54 of lateral tube 50 at junction 60.

For some applications, structural strut members 30 that define main tube 40 are arranged as a plurality of circumferential stent springs 88, each of which is shaped so as to define a plurality of stent cells 90. (It is to be understood that not all of structural strut members 30 that define main tube 40 necessarily are shaped so as to define stent springs 88; for some applications, only a portion of structural strut members 30 that define main tube 40 are shaped so as to define stent springs 88.) Typically, axially-adjacent ones of the stent springs are not in contact with one another, when stent-graft 20 is in the radially-expanded state. For some applications, stent cells 90 are diamond-shaped, when stent-graft 20 is in the radially-expanded state. For some applications, the diamond-shaped stent cells 90 have respective, different dimensions, when stent-graft 20 is in the radially-expanded state.

Typically, one of stent cells 90 of one of stent springs 88 is defined by the one or more of structural strut members 30 that completely surround proximal end 54 of lateral tube 50 at junction 60, when stent-graft 20 is in the radially-expanded state.

For some applications, a ratio of (a) an average circumference of main tube 40 and (b) an average circumference of lateral tube 50 is between 1:1 and 5:1, when stent-graft is in the radially-expanded state. For some applications, a length of lateral tube 50 is between 10% and 30% of an average circumference of lateral tube 50, when stent-graft 20 is in the radially-expanded state. For some applications, a circumference of lateral tube 50 at proximal end 54 of lateral tube 50 is between 5% and 30% greater than a circumference of lateral tube 50 at distal end 52 of lateral tube 50, when stent-graft 20 is in the radially-expanded state. For some applications, a length of main tube 40 is 4 to 15 cm.

For some applications, an angle between central longitudinal axis 64 of lateral tube 50 and a central longitudinal axis of main tube 40 is greater than 80 degrees, when stent-graft 20 is in the radially-expanded state. For some applications, an angle between central longitudinal axis 64 of lateral tube 50 and a longitudinal axis of main tube 40 is between 60 and 80 degrees, when stent-graft 20 is in the radially-expanded state. For some applications, an angle between central longitudinal axis 64 of lateral tube 50 and a longitudinal axis of main tube 40 is between 30 and 60 degrees, when stent-graft 20 is in the radially-expanded state.

For some applications, stent-graft 20 comprises two or more (e.g., exactly two or exactly three) lateral tubes 50, such as described hereinbelow with reference to FIGS. 3A-B, mutatis mutandis.

Figure 2A:
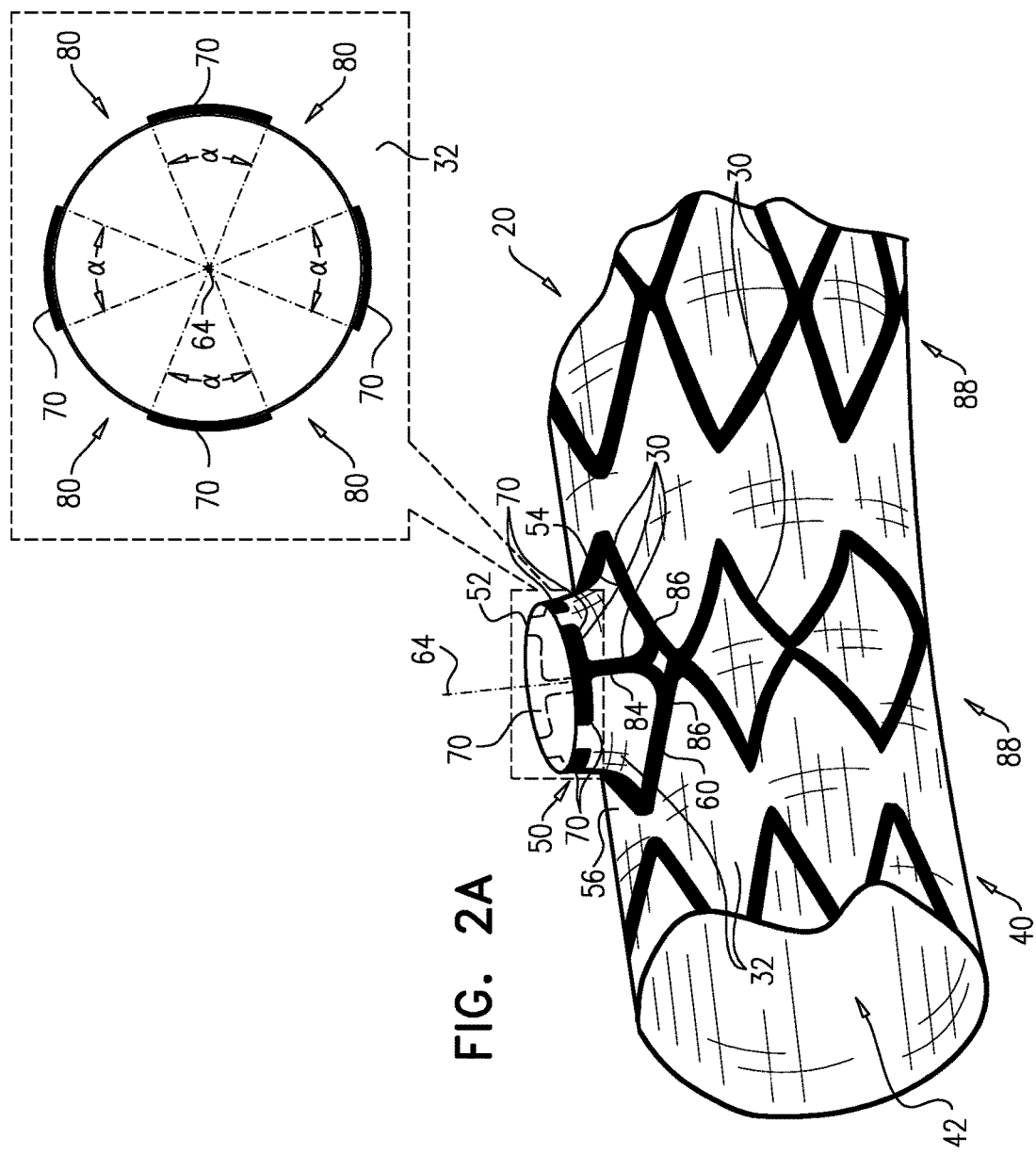
FIG. 2A is a schematic illustration of another configuration of the stent-graft of FIGS. 1A-B, in accordance with an application of the present invention.

Reference is now made to FIG. 2A, which is a schematic illustration of another configuration of stent-graft 20, in accordance with an application of the present invention. In this configuration, structural strut members 30 that define lateral tube 50 are shaped so as to define exactly four non-contiguous arcuate members 70, each of which subtends an angle α (alpha) around central longitudinal axis 64, such that they collectively subtend an angle equal to 4α (four times alpha). Arcuate members 70 are arranged so as to provide exactly four circumferential gaps 80.

Figure 2B:
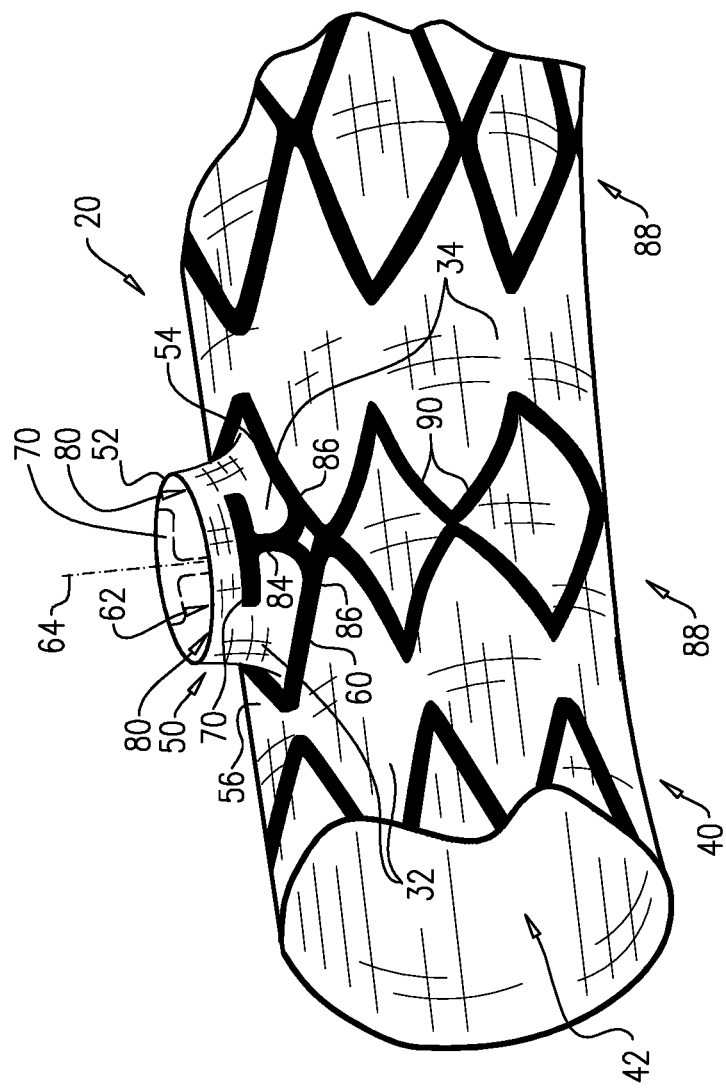
FIG. 2B, which is a schematic illustration of yet another configuration of stent-graft 20, in accordance with an application of the present invention.

Reference is now made to FIG. 2B, which is a schematic illustration of yet another configuration of stent-graft 20, in accordance with an application of the present invention. In this configuration, at least two of arcuate members 70 are disposed at respective different axial positions along lateral tube 50, when stent-graft 20 is in the radially-expanded state.

Figure 3A:
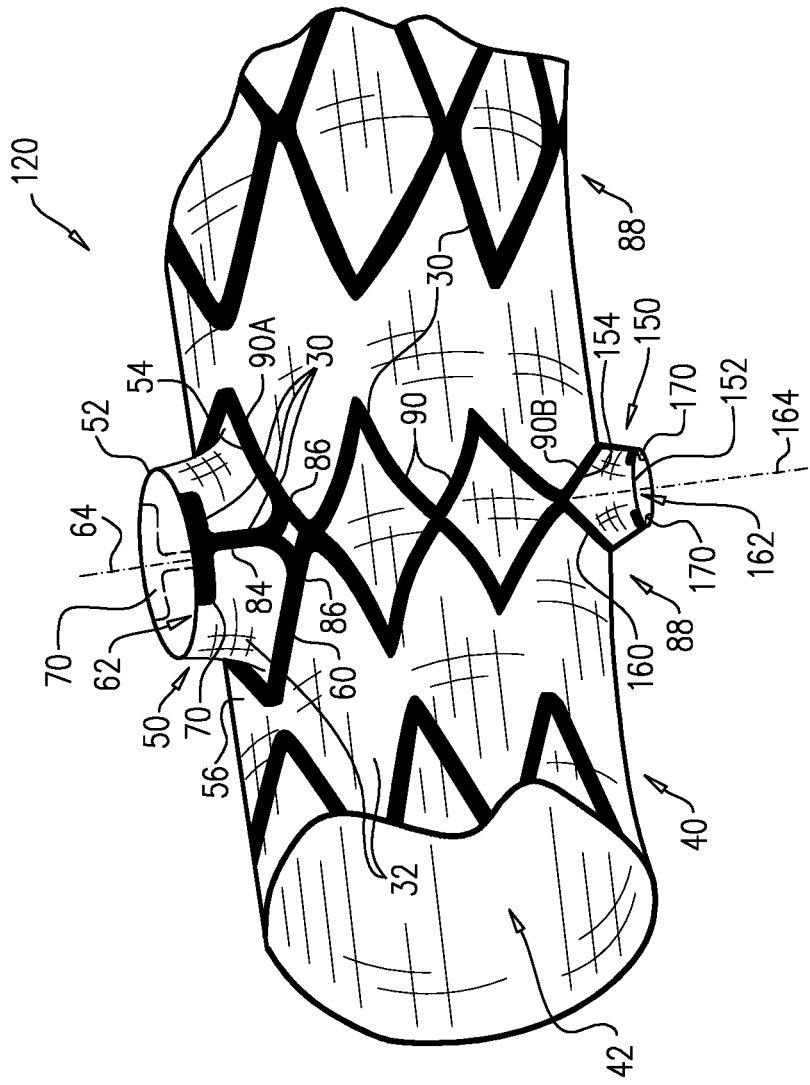
FIGS. 3A-B are schematic illustrations of a portion of another endovascular stent-graft, in accordance with an application of the present invention.
Figure 3B:
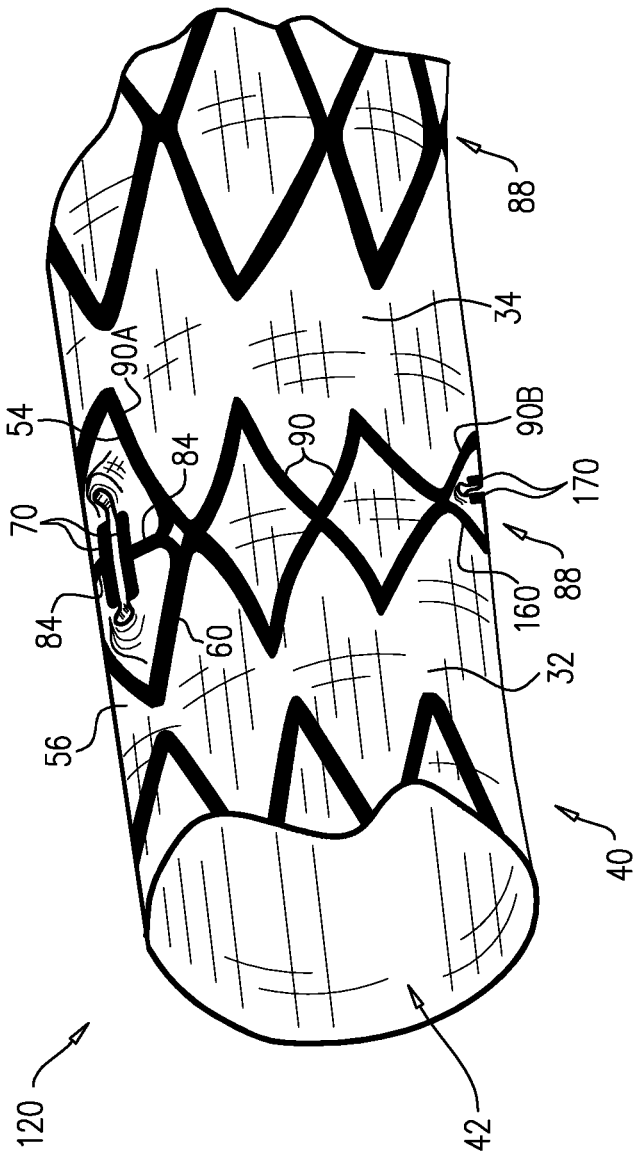

Reference is now made to FIGS. 3A and 3B, which are schematic illustrations of a portion of an endovascular stent-graft 120, in accordance with an application of the present invention. Other than as described below, stent-graft 120 is identical to stent-graft 20, described hereinabove with reference to FIGS. 1A-B and 2A-B, and may implement any of the features of stent-graft 20.

As mentioned above with reference to FIGS. 1A-B, for some applications, structural strut members 30 that define main tube 40 are arranged as a plurality of circumferential stent springs 88, each of which is shaped so as to define a plurality of stent cells 90. Typically, axially-adjacent ones of the stent springs are not in contact with one another, when stent-graft 20 is in the radially-expanded state. Typically, one of stent cells 90 of one of stent springs 88 is defined by the one or more of structural strut members 30 that completely surround proximal end 54 of lateral tube 50 at junction 60, when stent-graft 20 is in the radially-expanded state. For some applications, stent cells 90 are diamond-shaped, when stent-graft 20 is in the radially-expanded state. For some applications, the diamond-shaped stent cells 90 have respective, different dimensions, when stent-graft 20 is in the radially-expanded state.

In the configuration shown in FIGS. 3A-B, a largest one of stent cells 90 (labeled 90A) (e.g., the diamond-shaped stent cells) is at least 100% greater in surface area than a smallest one of stent cells 90 (labeled 90B) (e.g., the diamond-shaped stent cells), which largest one of stent cells 90A is the one of the stent cells 90 that is defined by the one or more of structural strut members 30 that completely surround proximal end 54 of lateral tube 50 at junction 60, when stent-graft 20 is in the radially-expanded state.

As mentioned above regarding stent-graft 20, for some applications, stent-graft 120 comprises two or more (e.g., exactly two or exactly three) lateral tubes 50. For these applications, lateral tube 50 is a first lateral tube 50, distal and proximal ends 52 and 54 are first distal and proximal ends 54 and 54, junction 60 is a first junction 60, lateral lumen 62 is a first lateral lumen 62, central longitudinal axis 64 is a first central longitudinal axis 64, and arcuate members 70 are first arcuate members 70. Structural strut members 30 and graft member 32 are arranged so as to define, when stent-graft 20 is in the radially-expanded state, a second lateral tube 150, which (a) has (i) a second distal end 152 and (ii) a second proximal end 154 that is joined to lateral wall 56 of main tube at a second junction 160, (b) is shaped so as to define a second lateral lumen 162 that is in fluid communication with main lumen 42, and (c) defines a second central longitudinal axis 164. When stent-graft 20 is in the radially-expanded state, structural strut members that define second lateral tube 150 are shaped so as to define two to four non-contiguous second arcuate members 170, which (a) are centered around second central longitudinal axis 164, and (c) collectively subtend at least 150 degrees around second central longitudinal axis 164.

For some applications, the smallest one of stent cells 90B (e.g., the diamond-shaped stent cells) completely surrounds second proximal end 154 of second lateral tube 150 at second junction 160, when stent-graft 20 is in the radially-expanded state. For some applications, an average circumference of second lateral tube 150 is less than an average circumference of first lateral tube 50.

Figure 6A:
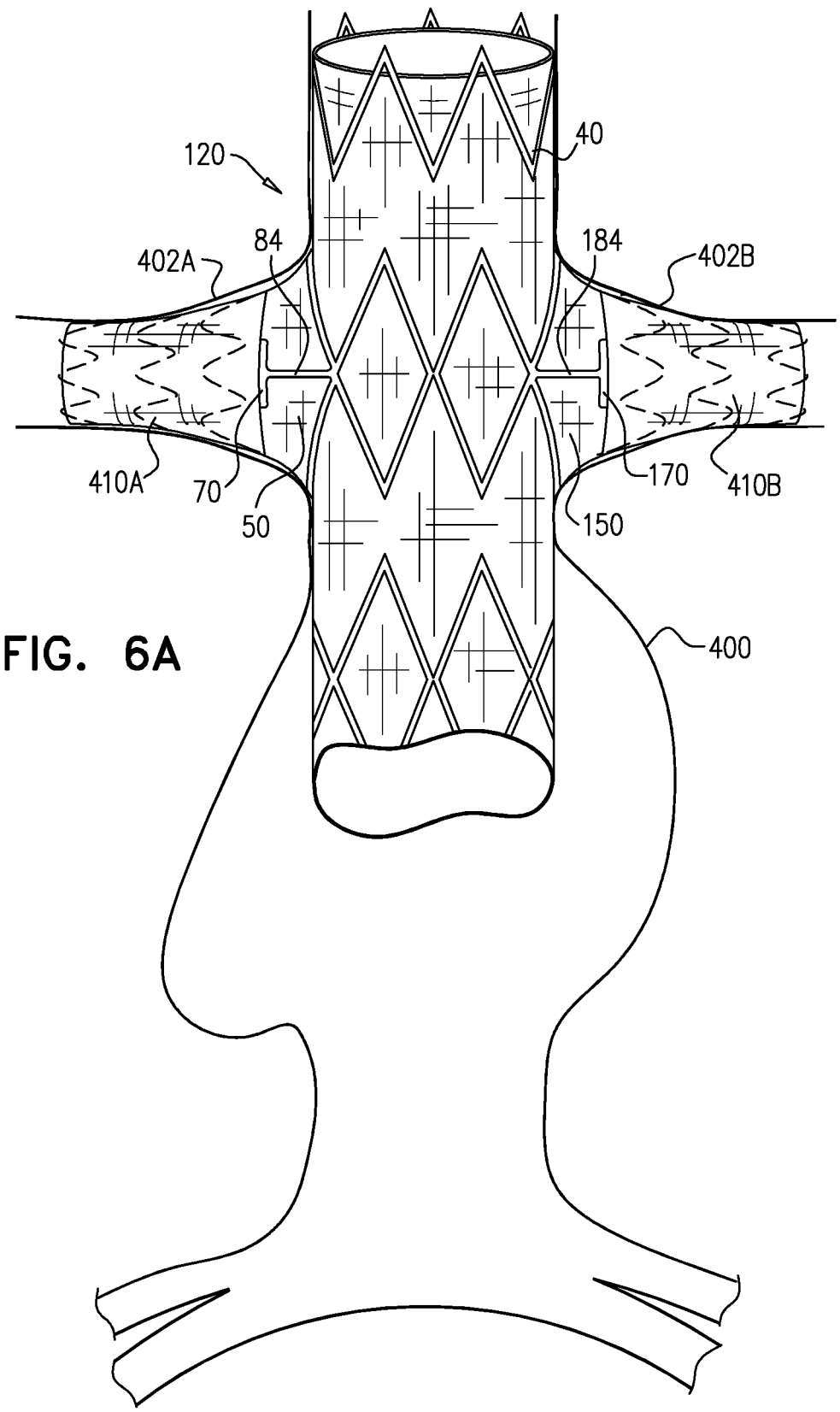
FIG. 6A-B are schematic illustrations of exemplary deployments of the stent-graft of FIGS. 3A-B, in accordance with respective applications of the present invention.
Figure 6B:
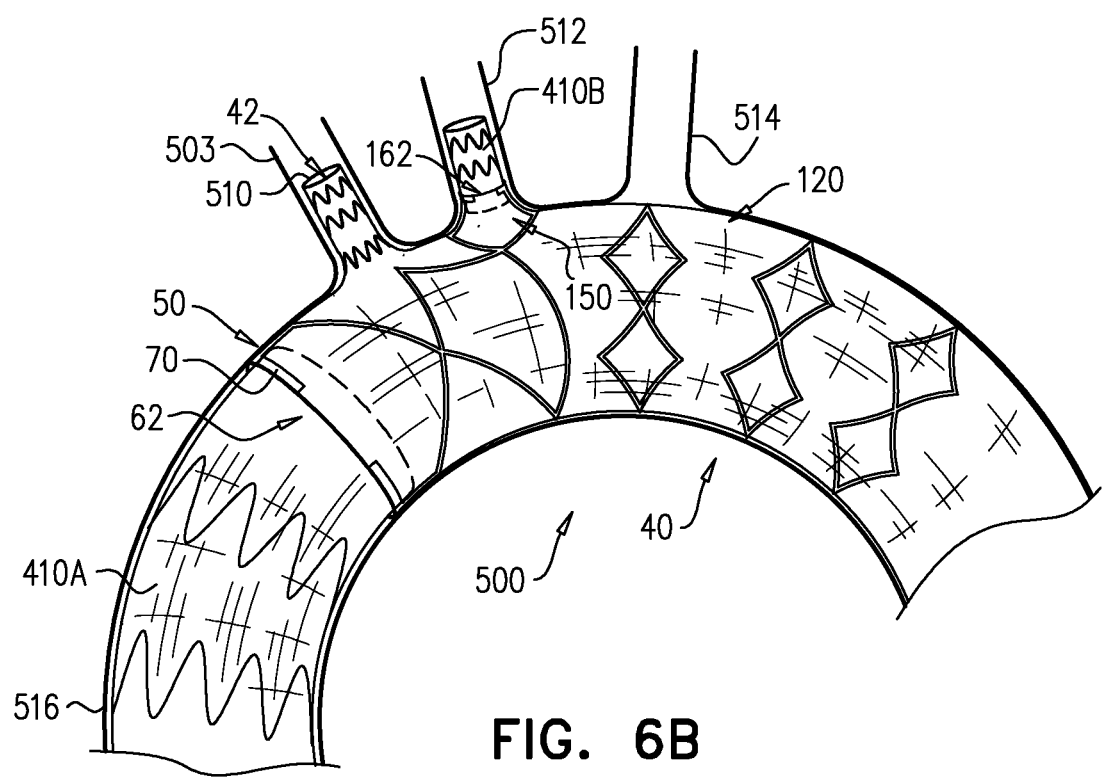

For other applications, such as shown in FIGS. 6A-B, structural strut members 30 and graft member 32 are arranged so as to define, when stent-graft 20 is in the radially-expanded state, second lateral tube 150, and the smallest one of stent cells 90B (e.g., the diamond-shaped stent cells) does not surround second proximal end 154 of second lateral tube 150 at second junction 160, when stent-graft 20 is in the radially-expanded state. For these applications, an average circumference of second lateral tube 150 may be equal to an average circumference of first lateral tube 50.

Figure 4A:
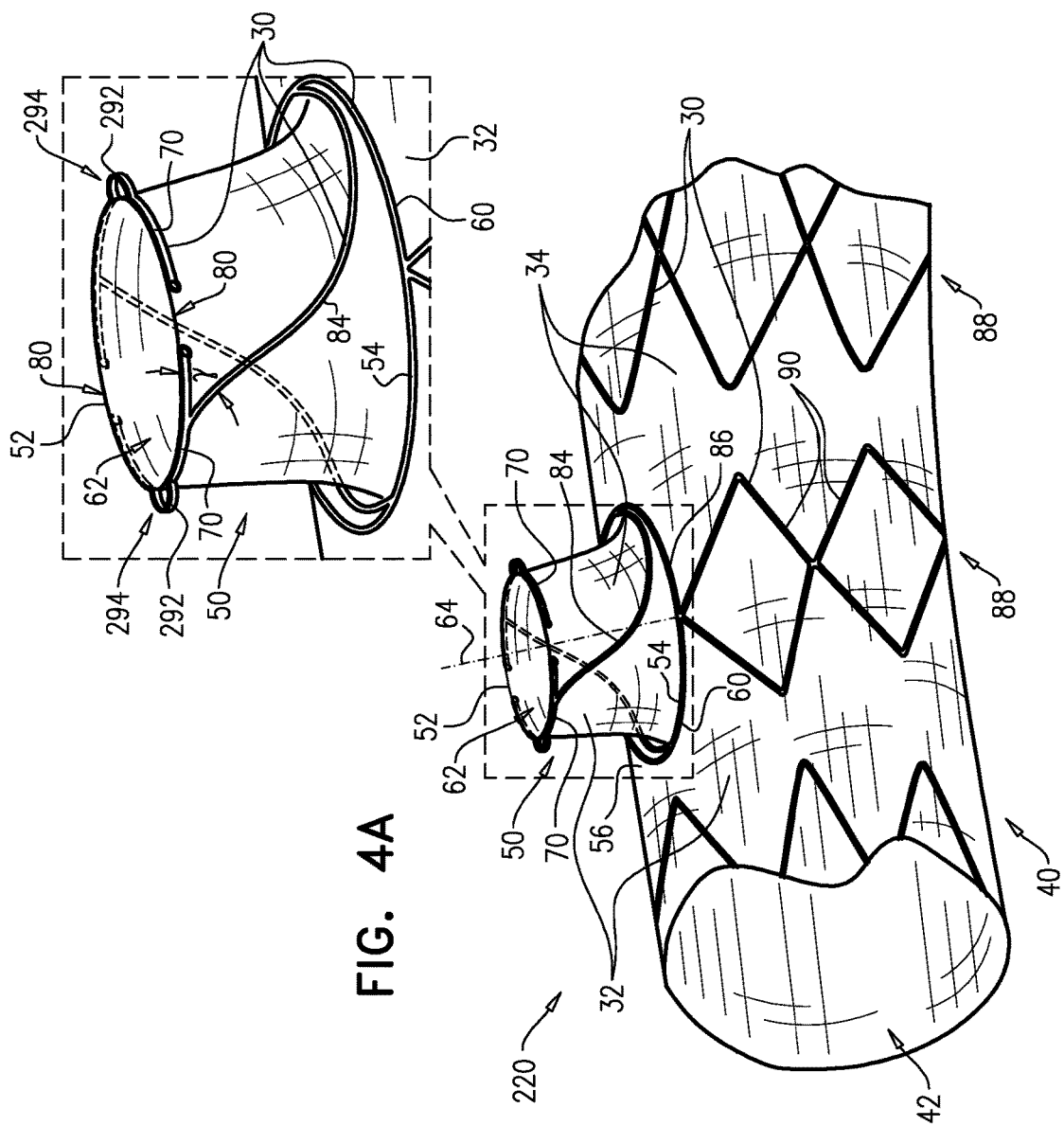
FIGS. 4A-B are schematic illustrations of a portion of yet another endovascular stent-graft, in accordance with an application of the present invention.
Figure 4B:
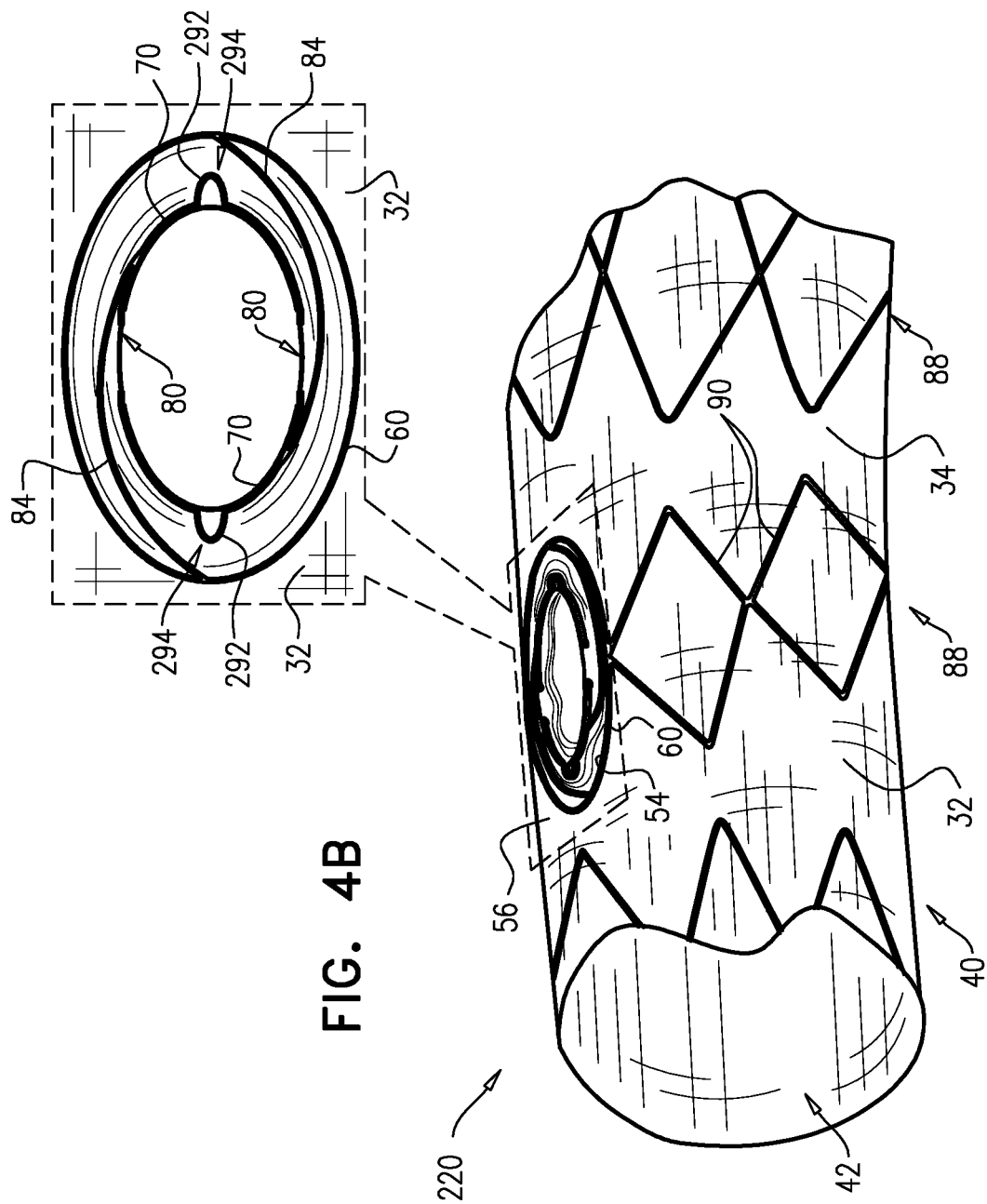

Reference is now made to FIGS. 4A and 4B, which are schematic illustrations of a portion of an endovascular stent-graft 220, in accordance with an application of the present invention. Stent-graft 220 may implement any of the features of stent-graft 20, described hereinabove with reference to FIGS. 1A-B and 2A-B, and/or stent-graft 120, described hereinabove with reference to FIGS. 3A-B.

As mentioned above, for some applications, structural strut members 30 that define lateral tube 50 are shaped so as to define respective linking members 84 for arcuate members 70, which linking members 84 link arcuate members 70 to junction 60, such as with the one or more structural strut members 86 that surround proximal end 54, for applications in which these surrounding strut members are provided. For some applications, such as shown in FIG. 4A, linking members 84 form respective angles γ (gamma) with the respective arcuate members 70, which angles have an average of 30 to 60 degrees (e.g., about 45 degrees), when stent-graft 20 is in the radially-expanded state. For some applications, proximal portions of linking members 84 are generally asymptotic with junction 60, and with the one or more structural strut members 86 that surround proximal end 54, for applications in which these surrounding strut members are provided.

In this configuration, distal end 52 of lateral tube 50 rotates during the transition from the compressed delivery state to the radially-expanded state. As a result, in the crimped configuration shown in FIG. 4B (in which lateral tube is in the radially-compressed state thereof), linking members 84 do not overlap one another, which might cause an increased crossing profile of stent-graft 220.

For some applications, one or more (e.g., all) of arcuate members 70 are shaped so as to define respective jointed locations 292, which are configured such that the arcuate members fold at the jointed locations 292 when main tube 40 is radially compressed. Without such folding protrusions, the arcuate members might plastically deform at arbitrary locations therealong when the main tube is radially compressed. For some applications, each of the jointed locations 292 is at a location along its respective arcuate member 70 that is within a number of degrees of a circumferential center 294 of the arcuate member around central longitudinal axis 64, which number of degrees is equal to 40% of a total number of degrees of the arcuate member, such as at the circumferential center of the arcuate member. For some applications, arcuate members 70 of stent-graft 20 or 120, described hereinabove with reference to FIGS. 1A-3B, are shaped so as to define respective jointed locations 292.

For some applications, stent-graft 220 comprises two or more (e.g., exactly two or exactly three) lateral tubes 50, such as described hereinbelow with reference to FIGS. 3A-B, mutatis mutandis.

Figure 5A:
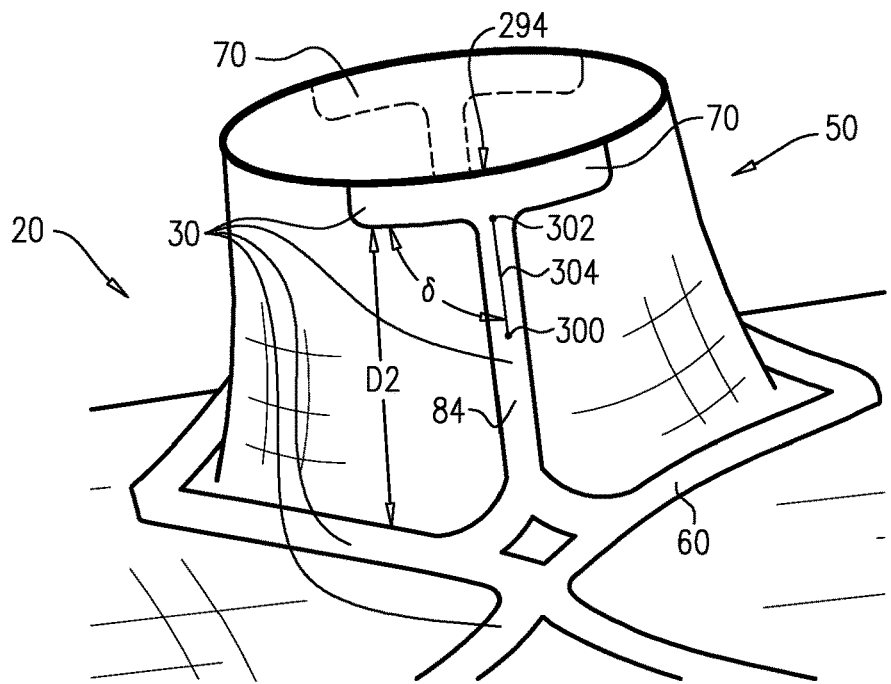
FIGS. 5A and 5B, which are schematic illustrations of portions of the stent-grafts of FIGS. 1A-B and 4A-B, respectively, in accordance with respective applications of the present invention.
Figure 5B:
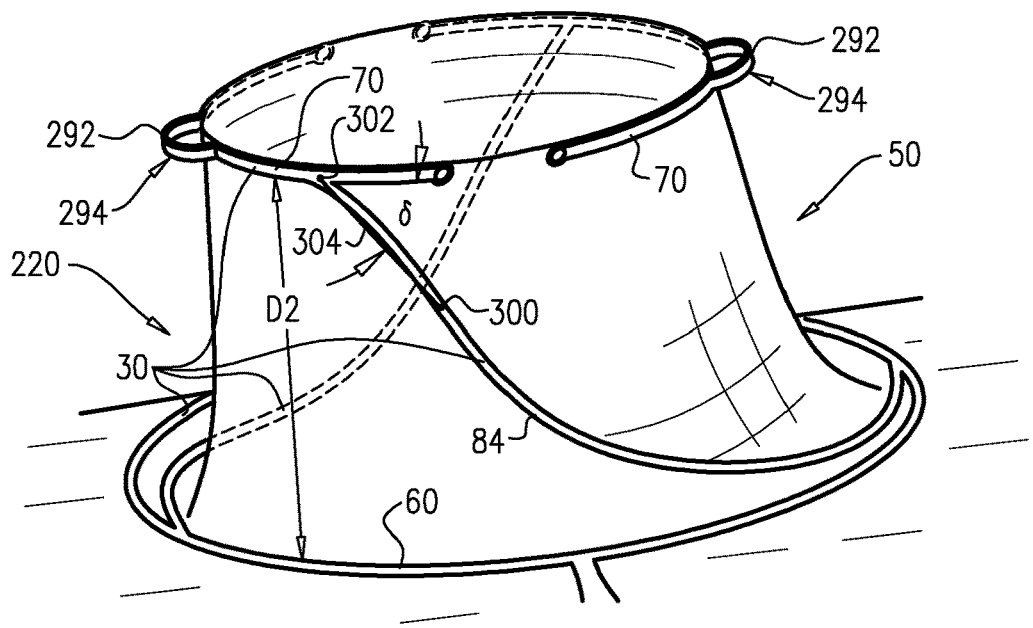

Reference is now made to FIGS. 5A and 5B, which are schematic illustrations of portions of stent-grafts 20 and 220, respectively, in accordance with respective applications of the present invention. As mentioned above, for some applications, structural strut members 30 that define lateral tube 50 are shaped so as to define respective linking members 84 for arcuate members 70, which linking members 84 link arcuate members 70 to junction 60.

For some applications, as shown in FIGS. 5A and 5B, when stent-graft 20 is in the radially-expanded state, respective points 300 on linking members 84 and respective juncture points 302 between linking members 84 and arcuate members 70 define respective lines 304 (it is to be understood that points 300 and 302 and lines 304 are not actual structural features of the stent-grafts, but are instead abstract geometric elements used to describe the physical properties of the device). Lines 304 form respective angles δ (delta) with the respective arcuate members 70. The angles δ (delta) have an average of to 90 degrees. Points 300 on linking members 84 are at 30% of a distance D2 between the axial position of arcuate members 70 and junction 60. For some applications, such as shown in FIG. 5A, the average is 85 to 90 degrees, e.g., 90 degrees, while for other applications, such as shown in FIG. 5B, the average is 30 to 60 degrees, e.g., about 45 degrees.

For some applications, such as labeled in FIG. 5A and also shown in FIGS. 1A, 2A, and 3A, juncture point 302 between each of the linking members 84 and its respective arcuate member is at a location along the arcuate member that is within a number of degrees of circumferential center 294 of the arcuate member around central longitudinal axis 64, which number of degrees is equal to 40% of a total number of degrees of the arcuate member, such as at the circumferential center of the arcuate member. For other applications, such as labeled in FIG. 5B and also shown in FIG. 4A, Reference is now made to FIGS. 6A-B, which are schematic illustrations of exemplary deployments of stent-graft 120, in accordance with respective applications of the present invention. Stent-graft 120, and the other stent-grafts described herein, may also be used to treat a blood vessel suffering from a dissection, or, more generally, a pathologically dilated aorta. The techniques described with reference to FIGS. 6A-B may also be used to deploy stent-grafts 20 and 220.

In the configuration shown in FIG. 6A, stent-graft 120 is shown deployed in the vicinity of a sub-renal (e.g., juxta-renal) abdominal aortic aneurysm 400 of an abdominal aorta. In this deployment, an average circumference of second lateral tube 150 is equal to an average circumference of first lateral tube 50.

In the configuration shown in FIG. 6B, stent-graft 120 is shown deployed in an aortic arch 500 and a brachiocephalic artery 503. More particularly, main tube 40 is shown deployed mostly in aortic arch 500, with a narrower proximal end 510 of the main tube deployed in brachiocephalic artery 503. For some applications, a circumference of proximal end 510 of main tube 40 is 3 to 10 cm, when stent-graft 120 is in the radially-expanded state. Alternatively or additionally, for some applications, a circumference of a distal end of main tube 40 is 6 to 12 cm, when stent-graft 120 is in the radially-expanded state. Alternatively, narrower proximal end 510 of main tube 40 may be configured to be disposed in another branch of aortic arch 500, such as a left common carotid artery 512 or a left subclavian artery 514. Optionally, the techniques described herein are used in combination with the techniques described in US Patent Application Publication 2013/0013050, which is incorporated herein by reference. (It is noted that in the deployment shown in FIG. 6B, blood flow to left subclavian artery 514 is blocked by stent-graft 120. The left subclavian artery is either "sacrificed" (i.e. via occlusion), or surgically anastomosed to left common carotid artery 512, or possibly to another source artery, such as the right common carotid artery. Alternatively, stent-graft 120 may be shaped so as to define an additional lateral tube 50, and an additional branching stent-graft may be deployed into left subclavian artery 514.)

The deployment is typically performed in a transvascular (typically percutaneous) procedure using one or more guidewires and an elongate delivery tube that is sized to hold stent-graft 120 in the radially-compressed delivery state. For some applications, a ratio of (a) an average circumference of main tube 40 when in the radially-expanded state thereof to (b) an inner circumference of the delivery tube is at least 5. Typically, after stent-graft 120 is positioned at the desired anatomical site, the sheath is withdrawn proximally, exposing stent-graft 120 and allowing the stent-graft to self-expand, or be expanded by plastic deformation using a balloon, into the radially-expanded state. The deployment may be performed using deployment techniques known in the art and/or described in any of the patent applications publications and patents incorporated hereinbelow by reference.

For some applications, such as shown in FIG. 6A, first and second lateral tubes 50 and 150 are positioned in respective branching blood vessels, such as branching visceral arteries, e.g., renal arteries 402A and 402B. For other applications, such as shown in FIG. 6B, one of first and second lateral tubes 50 and 150 is positioned in the main blood vessel and the other in a branching blood vessel, e.g., first lateral tube 50 is positioned in aortic arch 500, facing upstream, and second lateral tube 150 is positioned in brachiocephalic artery 503.

For some applications, two or more branching stent-grafts, such as two branching stent-grafts 410A and 410B, are deployed through a portion main lumen 42 of main tube and through first and second lateral lumens 62 and 162 of first and second lateral tubes 50 and 150, respectively, and into their respective arteries, so as to form respective blood-tight seals with first and second lateral tubes 50 and 150. For example, as shown in FIG. 6A, branching stent-grafts 410A and 410B are positioned in renal arteries 402A and 402B, respectively, or, as shown in FIG. 6B, branching stent-grafts 410A and 410B are positioned in an ascending aorta 516 and left common carotid artery 512, respectively. For example, the branching stent-grafts may be deployed using respective guidewires and cannulae, such as described in PCT Application PCT/IL2014/050973, filed Nov. 6, 2014, which published as WO 2015/075708, and which is incorporated herein by reference, with respect to FIGS. 13E-J thereof. As a result, in the deployment shown in FIG. 6A, stent-graft 120 and branching stent-grafts 410A and 410B together define a fluid flow path through the aorta and the renal arteries, and in the deployment shown in FIG. 6B, stent-graft 120 and branching stent-grafts 410A and 410B together define a fluid flow path through aortic arch 500 and brachiocephalic artery 503 and left common carotid artery 512. Typically, the branching stent-grafts are transvascularly introduced when in respective radially-compressed delivery states, and are transitioned to respective radially-expanded states.

As mentioned above, for some applications the stent-graft is shaped so as to define one or more additional lateral tubes 50. For these applications, one or more additional branching stent-grafts may be deployed into additional branching visceral arteries, such as, for the deployment shown in FIG. 6A, the superior mesenteric artery (SMA) and/or the celiac artery, or, for the deployment shown in FIG. 6B, left subclavian artery 514, and sealingly coupled to the additional lateral tube(s). Typically, a main stent-graft is deployed and blood-tightly sealingly coupled to a proximal end of stent-graft 120 to extend the fluid flow path past the aneurysm, such as shown in FIG. 13J of the above-mentioned PCT Application PCT/IL2014/050973, mutatis mutandis. Alternatively, stent-graft 120 may be shaped so as to define a fenestration to allow blood flow to the SMA.

The scope of the present invention includes embodiments described in the following patents and patent applications, which are assigned to the assignee of the present application and are incorporated herein by reference. In an embodiment, techniques and apparatus described in one or more of the following patent applications are combined with techniques and apparatus described herein. In particular, the stent-grafts described herein may be used as components of the stent-graft systems described in the following patent and patent applications, and deployed as described as described in the following patent and patent applications, mutatis mutandis.

PCT Application PCT/IL2008/000287, filed Mar. 5, 2008, which published as PCT Publication WO 2008/107885

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2011/000135, filed Feb. 8, 2011, which published as PCT Publication WO 2011/095979

PCT Application PCT/IL2012/000060, filed Feb. 2, 2012, which published as PCT Publication WO 2012/104842

PCT Application PCT/IL2012/000241, filed Jun. 19, 2012, which published as PCT Publication WO 2012/176187

PCT Application PCT/IL2012/000300, filed Aug. 12, 2012, which published as PCT Publication WO 2013/030819

U.S. Pat. No. 8,317,856 to Shalev et al.

U.S. Pat. No. 8,574,287 to Benary et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

U.S. application Ser. No. 13/031,871, filed Feb. 22, 2011, which published as US Patent Application Publication 2011/0208289

U.S. Provisional Application 61/496,613, filed Jun. 14, 2011

U.S. Provisional Application 61/499,195, filed Jun. 21, 2011

U.S. Provisional Application 61/505,132, filed Jul. 7, 2011

U.S. Provisional Application 61/529,931, filed Sep. 1, 2011

U.S. Provisional Application 61/553,209, filed Oct. 30, 2011

U.S. application Ser. No. 13/380,278, filed Dec. 22, 2011, which published as US Patent Application Publication 2012/0150274

U.S. application Ser. No. 13/384,075, filed Jan. 13, 2012, which published as US Patent Application Publication 2012/0179236

U.S. application Ser. No. 13/505,996, filed May 3, 2012, which published as US Patent Application Publication 2012/0310324

U.S. application Ser. No. 13/513,397, filed Jun. 1, 2012, which published as US Patent Application Publication 2012/0330399

U.S. application Ser. No. 13/514,240, filed Jun. 6, 2012, which published as US Patent Application Publication 2013/(X) 13051

U.S. Provisional Application 61/678,182, filed Aug. 1, 2012

U.S. application Ser. No. 13/577,161, filed Aug. 3, 2012, which published as US Patent Application Publication 2013/0035751

U.S. application Ser. No. 13/512,778, filed Sep. 24, 2012, which published as US Patent Application Publication 2013/0013050

U.S. application Ser. No. 13/807,880, filed Dec. 31, 2012, which published as US Patent Application Publication 2013/0131783

PCT Application PCT/IL2012/000095, filed Mar. 1, 2012, which published as PCT Publication WO 2012/117395

PCT Application PCT/IL2012000148, filed Apr. 4, 2012, which published as PCT Publication WO 2013/030818

PCT Application PCT/IL2012000190, filed May 15, 2012, which published as PCT Publication WO 2013/171730

PCT Application PCT/IL2012/000269, filed Jul. 2, 2012, which published as PCT Publication WO 2013/005207

PCT Application PCT/IL2012/050424, filed Oct. 29, 2012, which published as PCT Publication WO 2013/065040

PCT Application PCT/IL2012/050506, filed Dec. 4, 2012, which published as PCT Publication WO 2013/084235

U.S. Provisional Application 61/749,965, filed Jan. 8, 2013

U.S. application Ser. No. 13/807,906, filed Feb. 8, 2013, which published as US Patent Application Publication 2013/0204343

U.S. Provisional Application 61/775,964, filed Mar. 11, 2013

U.S. Provisional Application 61/826,544, filed May 23, 2013

U.S. application Ser. No. 13/979,551, filed Jul. 12, 2013, which published as US Patent Application Publication 2013/0289587

PCT Application PCT/IL2013/050656, filed Jul. 31, 2013, which published as PCT Publication WO 2014/020609

U.S. Provisional Application 61/906,014, filed Nov. 19, 2013

PCT Application PCT/IL2014/050019, filed Jan. 7, 2014, which published as PCT Publication WO 2014/108895

U.S. Provisional Application 61/926,533, filed Jan. 13, 2014

PCT Application PCT/IL2014/050174, filed Feb. 18, 2014, which published as PCT Publication WO 2014/141232

PCT Application PCT/IL2014/050434, filed May 18, 2014, which published as PCT Publication WO 2014/188412

PCT Application PCT/IL2014/050973, filed Nov. 6, 2014, which published as PCT Publication WO 2015/075708

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an endovascular stent-graft, which is configured to transition from a radially-compressed delivery state to a radially-expanded state, and which comprises:

a plurality of structural strut members; and a graft member, which comprises one or more substantially blood-impervious flexible sheets, and which is fixed to the structural strut members, wherein the structural strut members and the graft member are arranged so as to define, when the stent-graft is in the radially-expanded state:

a main tube, which is shaped so as to define a main lumen, and a lateral tube, which (a) has (i) a distal end and (ii) a proximal end that is joined to a lateral wall of the main tube at a junction, (b) is shaped so as to define a lateral lumen that is in fluid communication with the main lumen, and (c) defines a central longitudinal axis, and wherein, when the stent-graft is in the radially-expanded state, the structural strut members that define the lateral tube are shaped so as to define two to four non-contiguous arcuate members, which (a) are centered around the central longitudinal axis, (b) define respective arcs of a common circle, (c) collectively subtend at least 150 degrees around the central longitudinal axis, and (d) have respective pairs of arcuate-member ends, wherein all of the arcuate-member ends of all of the arcuate members are disposed at a same axial position along the lateral tube, wherein the same axial position is distal to the junction along the lateral tube.

2. The apparatus according to claim 1, wherein the arcuate members collectively subtend at least 180 degrees around the central longitudinal axis, when the stent-graft is in the radially-expanded state.

3. The apparatus according to claim 2, wherein the arcuate members collectively subtend at least 210 degrees around the central longitudinal axis, when the stent-graft is in the radially-expanded state.

4. The apparatus according to claim 1, wherein at least one of the arcuate members alone subtends at least 60 degrees around the central longitudinal axis, when the stent-graft is in the radially-expanded state.

5. The apparatus according to claim 1, wherein when the main tube is in a radially-expanded state thereof and the lateral tube is in a compressed delivery state thereof, the arcuate members define a portion of a generally tubular outer surface of the main tube.

6. The apparatus according to claim 1, wherein the apparatus further comprises a branching stent-graft, which is configured to form a blood-tight seal with the lateral tube, when the stent-graft is in the radially-expanded state and the branching stent-graft is in a radially-expanded state.

7. The apparatus according to claim 1, wherein a ratio of (a) an average circumference of the main tube and (b) an average circumference of the lateral tube is between 1:1 and 5:1, when the stent-graft is in the radially-expanded state.

8. The apparatus according to claim 1, wherein a length of the lateral tube is between 10% and 30% of an average circumference of the lateral tube, when the stent-graft is in the radially-expanded state.

9. The apparatus according to claim 1, wherein a circumference of the lateral tube at the proximal end of the lateral tube is between 5% and 30% greater than a circumference of the lateral tube at the distal end of the lateral tube, when the stent-graft is in the radially-expanded state.

10. The apparatus according to claim 1, wherein an angle between the central longitudinal axis of the lateral tube and a central longitudinal axis of the main tube is greater than 80 degrees, when the stent-graft is in the radially-expanded state.

11. The apparatus according to claim 1, wherein the main tube has proximal and distal ends, and wherein a circumference of the proximal end of the main tube is 3 to 10 cm, when the stent-graft is in the radially-expanded state.

12. The apparatus according to claim 11, wherein a circumference of the distal end of the main tube is 6 to 12 cm, when the stent-graft is in the radially-expanded state.

13. The apparatus according to claim 1, wherein the one or more flexible sheets comprise a material selected from the group consisting of: polyethylene terephthalate and expanded polytetrafluoroethylene (PTFE).

14. The apparatus according to claim 1, wherein the arcuate members are arranged so as to provide respective circumferential gaps between circumferentially-adjacent ones of the arcuate members, when the stent-graft is in the radially-expanded state.

15. The apparatus according to claim 14, wherein the arcuate members collectively subtend no more than 350 degrees around the central longitudinal axis, when the stent-graft is in the radially-expanded state.

16. The apparatus according to claim 14, wherein each of the circumferential gaps measures at least 10 degrees, when the stent-graft is in the radially-expanded state.

17. The apparatus according to claim 14, wherein respective areas of the lateral tube, which (a) circumferentially correspond with the gaps and (b) extend from the axial position of the arcuate members along at least 50% of a distance between the axial position of the arcuate members and the junction, are free from the structural strut members, when the stent-graft is in the radially-expanded state.

18. The apparatus according to claim 1, wherein the structural strut members that define the lateral tube are shaped so as to define respective linking members for the arcuate members, which linking members link the arcuate members to the junction.

19. The apparatus according to claim 18, wherein, when the stent-graft is in the radially-expanded state, the lateral tube is free from the structural strut members, except for the arcuate members and the linking members, in an area that (a) extends entirely around the central longitudinal axis and (b) extends from the distal end of the lateral tube along at least 50% of a distance between the distal end of the lateral tube and the junction.

20. The apparatus according to claim 19, wherein, when the stent-graft is in the radially-expanded state, the lateral tube is free from the structural strut members, except for the arcuate members, the linking members, and any of the structural strut members that surround the proximal end of the lateral tube at the junction.

21. The apparatus according to claim 18, wherein an average length of the linking members equals at least 80% of a length of the lateral tube, when the stent-graft is in the radially-expanded state.

22. The apparatus according to claim 18, wherein, when the stent-graft is in the radially-expanded state, respective linking-member points on the linking members and respective juncture points between the linking members and the arcuate members define respective lines, wherein the respective lines form respective angles with the respective arcuate members, wherein the respective angles have an average of 30 to 90 degrees, and wherein the respective linking-member points on the linking members are at 30% of a distance between an axial position of the arcuate members and the junction.

23. The apparatus according to claim 22, wherein an average length of the linking members equals at least 80% of a length of the lateral tube, when the stent-graft is in the radially-expanded state.

24. The apparatus according to claim 22, wherein the average of the respective angles is 85 to 90 degrees.

25. The apparatus according to claim 18, wherein the linking members form respective angles with the respective arcuate members, and wherein the respective angles have an average of 30 to 90 degrees, when the stent-graft is in the radially-expanded state.

26. The apparatus according to claim 25, wherein the average of the respective angels is 85 to 90 degrees.

27. The apparatus according to claim 18, wherein each of the linking members is connected to its respective arcuate member at a juncture point at a location along the arcuate member that is within a number of degrees of a circumferential center of the arcuate member around the central circumferential axis, which number of degrees is equal to 40% of a total number of degrees of the arcuate member.

28. The apparatus according to claim 27, wherein the location along the arcuate member is at the circumferential center of the arcuate member.

29. The apparatus according to claim 18, wherein, when the stent-graft is in the radially-expanded state, one or more of the structural strut members (a) completely surround the proximal end of the lateral tube at the junction and (b) are connected to the linking members.

30. The apparatus according to claim 1, wherein one or more of the structural strut members completely surround the proximal end of the lateral tube at the junction, when the stent-graft is in the radially-expanded state.

31. The apparatus according to claim 30,
wherein the structural strut members that define the main tube are shaped so as a plurality of circumferential stent springs, each of which is shaped so as to define a plurality of stent cells, and
wherein one of the stent cells of one of the circumferential stent springs is defined by the one or more of the structural strut members that completely surround the proximal end of the lateral tube at the junction, when the stent-graft is in the radially-expanded state.

32. The apparatus according to claim 31, wherein the stent cells of the one of the circumferential stent springs are diamond-shaped, when the stent-graft is in the radially-expanded state.

33. The apparatus according to claim 32, wherein the diamond-shaped stent cells have respective, different dimensions, when the stent-graft is in the radially-expanded state.

34. The apparatus according to claim 33, wherein a largest one of the diamond-shaped stent cells is at least 100% greater in surface area than a smallest one of the diamond-shaped stent cells, which largest one of the diamond-shaped stent cells is the one of the stent cells that is defined by the one or more of the structural strut members that completely surround the proximal end of the lateral tube at the junction, when the stent-graft is in the radially-expanded state.

35. The apparatus according to claim 34,
wherein the lateral tube is a first lateral tube, the distal and proximal ends are first distal and proximal ends, the junction is a first junction, the lateral lumen is a first lateral lumen, the central longitudinal axis is a first central longitudinal axis, and the arcuate members are first arcuate members,
wherein the structural strut members and the graft member are arranged so as to define, when the stent-graft is in the radially-expanded state, a second lateral tube, which (a) has (i) a second distal end and (ii) a second proximal end that is joined to the lateral wall of the main tube at a second junction, (b) is shaped so as to define a second lateral lumen that is in fluid communication with the main lumen, and (c) defines a second central longitudinal axis,
wherein, when the stent-graft is in the radially-expanded state, the structural strut members that define the second lateral tube are shaped so as to define two to four non-contiguous second arcuate members, which (a) are centered around the second central longitudinal axis, and (b) collectively subtend at least 150 degrees around the second central longitudinal axis, and
wherein the smallest one of the diamond-shaped stent cells completely surrounds the second proximal end of the second lateral tube at the second junction, when the stent-graft is in the radially-expanded state.

36. A method for treating a subject, comprising:
transvascularly introducing an endovascular stent-graft into a blood vessel of the subject while the stent-graft is in a radially-compressed delivery state, which stent-graft comprises (a) a plurality of structural strut members, and (b) a graft member, which comprises one or more substantially blood-impervious flexible sheets, and which is fixed to the structural strut members; and
transitioning the stent-graft to a radially-expanded state, in which:
the structural strut members and the graft member are arranged so as to define (x) a main tube, which is shaped so as to define a main lumen, and (y) a lateral tube, which (a) has (i) a distal end and (ii) a proximal end that is joined to a lateral wall of the main tube at a junction, (b) is shaped so as to define a lateral lumen that is in fluid communication with the main lumen, and (c) defines a central longitudinal axis, and
the structural strut members that define the lateral tube are shaped so as to define two to four non-contiguous arcuate members, which (a) are centered around the central longitudinal axis, (b) define respective arcs of a common circle, (c) collectively subtend at least 150 degrees around the central longitudinal axis, and (d) have respective pairs of arcuate-member ends, wherein all of the arcuate-member ends of all of the arcuate members are disposed at a same axial position along the lateral tube, wherein the same axial position is distal to the junction along the lateral tube.

37. The apparatus according to claim 1, wherein the arcuate members are disposed with 3 mm of a distal end of a portion of the graft member that defines the lateral tube, when the stent-graft is in the radially-expanded state.

38. The apparatus according to claim 1, wherein an angle between the central longitudinal axis of the lateral tube and a central longitudinal axis of the main tube is between 60 and 80 degrees, when the stent-graft is in the radially-expanded state.

39. The apparatus according to claim 1, wherein an angle between the central longitudinal axis of the lateral tube and a central longitudinal axis of the main tube is between 30 and 60 degrees, when the stent-graft is in the radially-expanded state.

* * * * *